(12) United States Patent
Miyazaki et al.

(10) Patent No.: US 8,841,458 B2
(45) Date of Patent: Sep. 23, 2014

(54) COMPOUND CONTAINING PYRIDINE RING AND METHOD FOR PRODUCING HALOGENATED PICOLINE DERIVATIVE AND TETRAZOLYLOXIME DERIVATIVE

(75) Inventors: Hidekazu Miyazaki, Takaoka (JP); Satoru Yanaka, Odawara (JP); Shiro Tsubokura, Takaoka (JP); Tadashi Sugiura, Odawara (JP); Kaoru Noda, Takaoka (JP); Kengo Suzuki, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/583,733

(22) PCT Filed: Mar. 11, 2011

(86) PCT No.: PCT/JP2011/055809
§ 371 (c)(1),
(2), (4) Date: Sep. 10, 2012

(87) PCT Pub. No.: WO2011/111831
PCT Pub. Date: Sep. 15, 2011

(65) Prior Publication Data
US 2013/0012713 A1    Jan. 10, 2013

(30) Foreign Application Priority Data

Mar. 12, 2010 (JP) ................. 2010-056718
May 19, 2010 (JP) ................. 2010-115703
Jun. 2, 2010 (JP) ................. 2010-127207

(51) Int. Cl.
*C07D 213/75* (2006.01)
*C07D 401/12* (2006.01)
*C07D 405/12* (2006.01)

(52) U.S. Cl.
CPC .......... *C07D 213/75* (2013.01); *C07D 401/12* (2013.01); *C07D 405/12* (2013.01)
USPC ........................................ 546/309

(58) Field of Classification Search
None
See application file for complete search history.

(56) References Cited

U.S. PATENT DOCUMENTS

| | | | |
|---|---|---|---|
| 5,872,136 A | 2/1999 | Anthony et al. | |
| 8,119,646 B2 | 2/2012 | Christian et al. | |
| 2009/0098189 A1 | 4/2009 | Buchmann et al. | |
| 2010/0130738 A1 | 5/2010 | Kohno et al. | |
| 2010/0160335 A1 | 6/2010 | Kohno et al. | |
| 2011/0054172 A1 | 3/2011 | Iwamura et al. | |
| 2013/0023664 A1 | 1/2013 | Kutose et al. | |

FOREIGN PATENT DOCUMENTS

| | | |
|---|---|---|
| CN | 101489390 A | 7/2009 |
| EP | 1982982 A1 | 10/2008 |
| GB | 2 279 346 A | 1/1995 |
| JP | 56-043268 A | 4/1981 |
| JP | 07-017948 A | 1/1995 |
| JP | 08-259539 A | 10/1996 |
| JP | 2003-137875 A | 5/2003 |
| JP | 2004-131392 A | 4/2004 |
| JP | 2004-131416 A | 4/2004 |
| JP | 2009-040711 A | 2/2009 |
| JP | 2011-012088 A | 1/2011 |
| RU | 2314294 C2 | 1/2008 |
| WO | WO 03/016303 A1 | 2/2003 |
| WO | WO 2007/141473 A1 | 12/2007 |
| WO | WO 2008/106692 A1 | 9/2008 |
| WO | WO 2008/156094 A1 | 12/2008 |
| WO | WO 2008/156102 A1 | 12/2008 |
| WO | WO 2009/014100 A1 | 1/2009 |
| WO | WO 2009/020191 A1 | 2/2009 |
| WO | WO 2009/113600 A1 | 9/2009 |
| WO | WO 2009/130900 A1 | 10/2009 |
| WO | WO 2010/000841 A1 | 1/2010 |
| WO | WO 2011/125568 A1 | 10/2011 |

OTHER PUBLICATIONS

Ijuin et al, Bioorganic & Medicinal Chemistry (2006), 14(10), pp. 3563-3570.*
Decision of Grant dated Dec. 9, 2013, in RU 2012138410, with English translation, 20 pages.
Office Action dated Dec. 17, 2013, in JP 2012-504543, with English translation, 8 pages.
New Experimental Chemistry, 14, Synthesis and Reaction of Organic Composition V, Maruzen Company, Limited, 1978, 2555-2569, with Partial English translation of p. 2555.
Bieber et al., "Silver catalyzed zinc Barbier reaction of benzylic halides in water," Tetrahedron Letters, Dec. 17, 1998, 39(51):9393-9396.
European Search Report dated Mar. 18, 2014 in EP 14000069.6.
European Search Report dated Mar. 18, 2014 in EP 14000071.2.
European Search Report dated Mar. 18, 2014 in EP 14000070.4.

* cited by examiner

*Primary Examiner* — Zinna Northington Davis
(74) *Attorney, Agent, or Firm* — Foley & Lardner LLP

(57) ABSTRACT

Disclosed is a compound containing a pyridine ring that can be synthesized in an industrially advantageous manner, and is useful as an intermediate for producing tetrazolyloxime derivatives that exhibit fungicidal activity (wherein $R^0$ represents a $C_{1-6}$ alkoxy group, $C_{1-6}$ alkoxy-$C_{1-6}$ alkoxy group or the like, $R^1$ represents a $C_{1-2}$ alkoxycarbonyl group, acetyl group or the like, Z represents a halogen atom, cyano group or the like, X represents a halogen atom, and n represents an integer of 0 to 3), and industrially advantageous production methods for producing 2-substituted amino-6-halomethylpyridine derivatives and tetrazolyloxime derivatives.

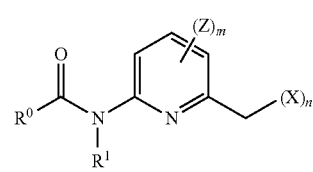

(1)

5 Claims, No Drawings

COMPOUND CONTAINING PYRIDINE RING AND METHOD FOR PRODUCING HALOGENATED PICOLINE DERIVATIVE AND TETRAZOLYLOXIME DERIVATIVE

CONTINUING DATA

This application is a 371 of PCT/JP2011/055809 filed Mar. 11, 2011.

TECHNICAL FIELD

The present invention relates to (1) a compound containing a pyridine ring that is ideal as an agrochemical intermediate, (2) a production method that enables a 2-substituted amino-6-halomethylpyridine derivative, which is useful as a synthetic intermediate for agrochemicals and the like, to be obtained in high yield, and (3) an industrially advantageous method for producing a tetrazolyloxime derivative that exhibits a superior antagonistic effect against plant diseases.

Priority is claimed on Japanese Patent Application No. 2010-056718, filed Mar. 12, 2010, Japanese Patent Application No. 2010-127207, filed Jun. 2, 2010, and Japanese Patent Application No. 2010-115703, filed May 19, 2010, the contents of which are incorporated herein by reference.

BACKGROUND ART

Examples of methods for producing halomethylpyridine derivatives include a method disclosed in Patent Document 1, in which 2-chloro-5-chloromethylpyridine is produced by adding a chlorinating agent such as oxalyl chloride dropwise to an acetonitrile solution of 2-chloro-5-acetaminomethylpyridine and dimethylformamide, and then heating the mixture at 80° C.

Patent Document 2 discloses a method for producing chloromethylpyridines by reacting an aminomethylpyridine with a nitrosating agent or a diazotizing agent, in the presence of a diluent, and if necessary in the presence of hydrogen chloride, and at a temperature within a range from −20° C. to +50° C.

Further, Patent Document 3 discloses a method for producing 6-chloro-2-(chloromethyl)pyridine that features reducing 6-chloro-2-(trichloromethyl)pyridine or 6-chloro-2-(dichloromethyl)pyridine.

[Chemical Formula 1]

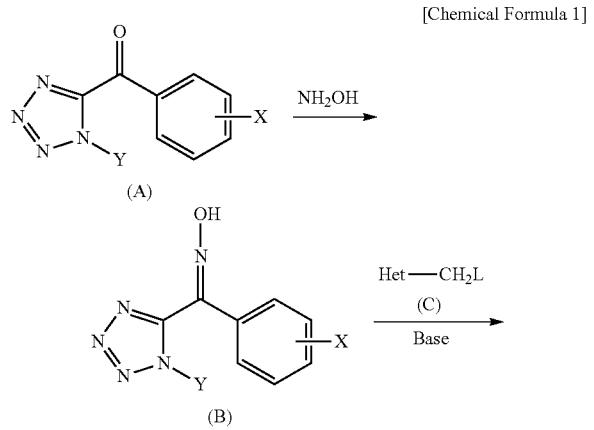

The tetrazolyloxime derivatives disclosed in Patent Document 4 and the like exhibit excellent fungicidal activity, and are viewed as promising compounds for the active ingredients of plant disease control agents. A method that has been disclosed for producing such tetrazolyloxime derivatives involves reacting a tetrazolylmethanone derivative represented by formula (A) with hydroxylamine to obtain a tetrazolylhydroxyimino derivative represented by formula (B), and subsequently reacting the tetrazolylhydroxyimino derivative with a compound represented by formula (C) in the presence of a base, thereby obtaining a tetrazolyloxime derivative represented by formula (D).

In relation to the present invention, Patent Documents 1 to 3 disclose methods for producing halomethylpyridine derivatives. Further, Patent Documents 4 and 5 disclose tetrazolyloxime derivatives having structures that are similar to that of the compound of the present invention, and these tetrazolyloxime derivatives have been proposed for use as fungicides.

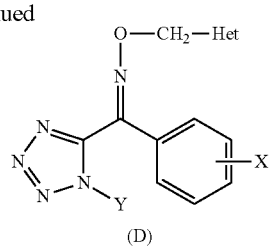

DOCUMENTS OF RELATED ART

Patent Documents

[Patent Document 1]
Japanese Unexamined Patent Application, First Publication No. Hei 08-259539
[Patent Document 2]
Japanese Unexamined Patent Application, First Publication No. Hei 07-017948
[Patent Document 3]
Japanese Unexamined Patent Application, First Publication No. Sho 56-43268
[Patent Document 4]
Japanese Unexamined Patent Application, First Publication No. 2003-137875
[Patent Document 5]
International Patent Publication No. WO 2003/016303

DISCLOSURE OF INVENTION

Problems to be Solved by the Invention

The present invention has an object of providing (1) a compound containing a pyridine ring that is ideal as an agrochemical intermediate, (2) a production method that enables a 2-substituted amino-6-halomethylpyridine derivative, which is useful as a synthetic intermediate for agrochemicals and the like, to be obtained in high yield, and (3) an industrially advantageous method for producing a tetrazolyloxime derivative that exhibits a superior antagonistic effect against plant diseases.

Means to Solve the Problems

The inventors of the present invention conducted intensive investigations aimed at achieving the above object. As a result, they discovered (1) that a compound containing a pyridine ring and having a specific structure could be synthesized in an industrially advantageous manner, and was useful as an intermediate in producing a tetrazolyloxime derivative that exhibits fungicidal activity, (2) that by reacting a 2-substituted amino-6-methylpyridine derivative and a brominating agent within an organic solvent, and then reacting the thus obtained reaction product with a phosphite ester and a base within an organic solvent, a 2-substituted amino-6-bromomethylpyridine derivative could be produced in high yield, and (3) that by reacting a specific 2-substituted amino-6-halomethylpyridine derivative and a tetrazolylhydroxyimino derivative, a novel production intermediate composed of a tetrazolyloxime derivative could be obtained, and that by reacting a specific 2-substituted amino-6-halomethylpyridine derivative and a tetrazolylhydroxyimino derivative, and then treating the thus obtained reaction product with a base, a tetrazolyloxime derivative that exhibits a superior antagonistic effect against plant diseases could be obtained in an industrially advantageous manner. The present invention was completed as a result of conducting further investigations based on these findings.

In other words, the present invention includes the aspects described below.

[1] A compound containing a pyridine ring, represented by formula (1):

[Chemical Formula 2]

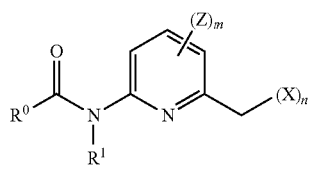

(1)

wherein $R^0$ represents a $C_{1-6}$ alkoxy group, $C_{1-6}$ alkoxy-$C_{1-6}$ alkoxy group, $C_{1-6}$ alkoxy-$C_{1-6}$ alkyl group, 1,3-dioxane-2-yl-$C_{1-6}$ alkyl group, or $CR^{O1}C(=NOR^{O2})$ group (wherein each of $R^{O1}$ and $R^{O2}$ independently represents a $C_{1-6}$ alkyl group), $R^1$ represents a $C_{1-2}$ alkoxycarbonyl group, an acetyl group, or a benzoyl group that may be substituted with a nitro group, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), m represents the number of Z substituents and is an integer of 0 to 3, and when m is 2 or more, the plurality of Z substituents may be the same as, or different from, each other, X represents a halogen atom, and n represents the number of X substituents and is an integer of 0 to 3, and when n is 2 or more, the plurality of X atoms may be the same as, or different from, each other.

[2] A method for producing a halogenated picoline derivative represented by formula (3), the method including a step B1 of reacting a compound represented by formula (2) and a halogenating agent within an organic solvent, and a step B2 of reducing the reaction product obtained in the step 131,

[Chemical Formula 3]

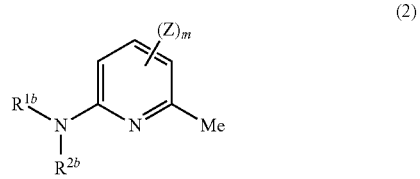

(2)

wherein $R^{1b}$ represents an unsubstituted or substituent-containing alkoxycarbonyl group, $R^{2b}$ represents an unsubstituted or substituent-containing alkoxycarbonyl group, unsubstituted or substituent-containing acyl group, unsubstituted or substituent-containing aryloxycarbonyl group, or unsubstituted or substituent-containing heterocyclic oxycarbonyl group, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), and m represents the number of Z substituents and is an integer of 0 to 3, and when m is 2 or more, the plurality of Z substituents may be the same as, or different from, each other,

[Chemical Formula 4]

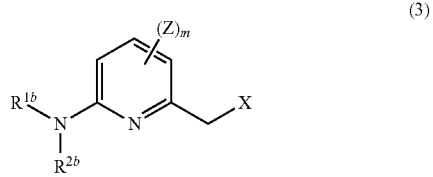

(3)

wherein $R^{1b}$, $R^{2b}$, Z and m are the same as defined above, and X represents a halogen atom.

[3] The method for producing a halogenated picoline derivative according to [2] above, wherein the step B1 is performed in the presence of a base.

[4] The method for producing a halogenated picoline derivative according to [2] or [3] above, wherein the organic solvent in the step B1 is benzene or a halogenated hydrocarbon.

[5] The method for producing a halogenated picoline derivative according to [2] or [3] above, wherein the step B2 is performed in the presence of a phase transfer catalyst.

[6] The method for producing a halogenated picoline derivative according to [2] or [3] above, wherein the halogenating agent is a brominating agent, and X represents a bromine atom.

[7] A method for producing a brominated picoline derivative represented by formula (6), the method including reacting a brominated picoline derivative represented by formula (4) and/or formula (5), a phosphite ester, and a base within an organic solvent,

[Chemical Formula 5]

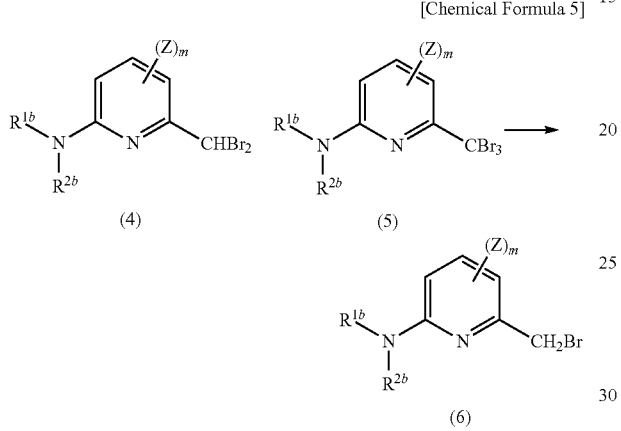

wherein $R^{1b}$ represents an unsubstituted or substituent-containing alkoxycarbonyl group, $R^{2b}$ represents an unsubstituted or substituent-containing alkoxycarbonyl group, unsubstituted or substituent-containing acyl group, unsubstituted or substituent-containing aryloxycarbonyl group, or unsubstituted or substituent-containing heterocyclic oxycarbonyl group, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), and m represents the number of Z substituents and is an integer of 0 to 3, and when m is 2 or more, the plurality of Z substituents may be the same as, or different from, each other.

[8] A method for producing a tetrazolyloxime derivative represented by formula (10), the method including a step C1 of reacting a halogenated picoline derivative represented by formula (7) with a tetrazolylhydroxyimino derivative represented by formula (8) to obtain a tetrazolyloxime derivative represented by formula (9), and a step C2 of treating the tetrazolyloxime derivative represented by formula (9) obtained in the step C1 with a base,

[Chemical Formula 6]

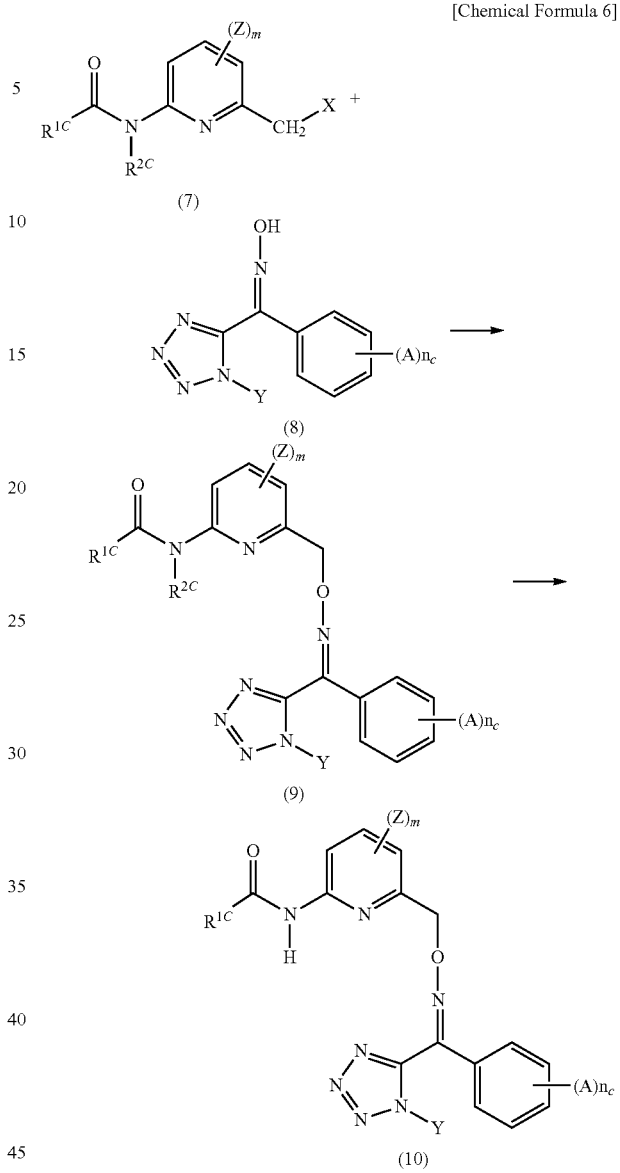

wherein within formula (7), $R^{1C}$ represents an unsubstituted or substituent-containing alkyl group, or an unsubstituted or substituent-containing alkoxy group, $R^{2C}$ represents an unsubstituted or substituent-containing alkoxycarbonyl group, or an unsubstituted or substituent-containing acyl group, X represents a halogen atom, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), and m represents the number of Z substituents and is an integer of 0 to 3, and when m is 2 or more, the plurality of Z substituents may be the same as, or different from, each other, and within formula (8), Y represents an unsubstituted or substituent-containing alkyl group, A represents a halogen atom, unsubstituted or substituent-containing alkyl group, unsubstituted or substituent-containing alkoxy group, cyano group, unsubstituted or substituent-containing alkylsulfonyl group, nitro group, or unsubstituted or substituent-containing aryl group, and $n_c$ represents the number of A substituents and is an integer of 0 to 5, and when $n_c$ is 2 or more, the plurality of the A substituents may be the same as, or different from, each other.

[9] A tetrazolyloxime derivative represented by formula (9):

[Chemical Formula 7]

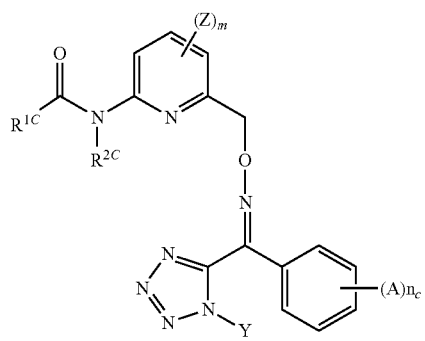

(9)

wherein $R^{1C}$ represents an unsubstituted or substituent-containing alkyl group, or an unsubstituted or substituent-containing alkoxy group, $R^{2C}$ represents an unsubstituted or substituent-containing alkoxycarbonyl group, or an unsubstituted or substituent-containing acyl group, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), m represents the number of Z substituents and is an integer of 0 to 3, and when m is 2 or more, the plurality of Z substituents may be the same as, or different from, each other, Y represents an unsubstituted or substituent-containing alkyl group, A represents a halogen atom, unsubstituted or substituent-containing alkyl group, unsubstituted or substituent-containing alkoxy group, cyano group, unsubstituted or substituent-containing alkylsulfonyl group, nitro group, or unsubstituted or substituent-containing aryl group, and $n_c$ represents the number of A substituents and is an integer of 0 to 5, and when $n_c$ is 2 or more, the plurality of the A substituents may be the same as, or different from, each other.

[10] A method for producing a tetrazolyloxime derivative represented by formula (9), the method including a step C1 of reacting a halogenated picoline derivative represented by formula (7) with a tetrazolylhydroxyimino derivative represented by formula (8),

[Chemical Formula 8]

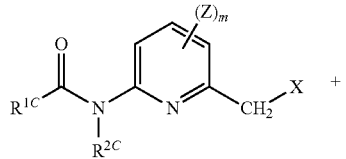

(7)

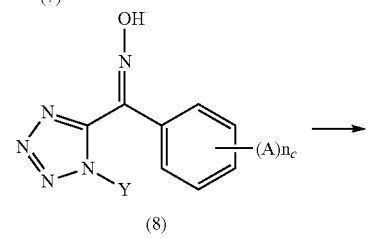

(8)

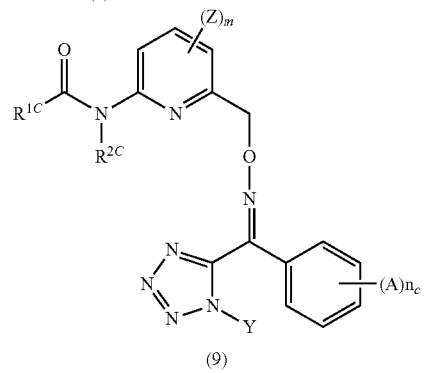

(9)

wherein $R^{1C}$ represents an unsubstituted or substituent-containing alkyl group, or an unsubstituted or substituent-containing alkoxy group, $R^{2C}$ represents an unsubstituted or substituent-containing alkoxycarbonyl group, or an unsubstituted or substituent-containing acyl group, X represents a halogen atom, Z represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$ (wherein $R^3$ represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group, and p represents the number of oxygen atoms shown in the parentheses, and is an integer of 0 to 2), m represents the number of Z substituents and is an integer of 0 to 3, and when m is 2 or more, the plurality of Z substituents may be the same as, or different from, each other, Y represents an unsubstituted or substituent-containing alkyl group, A represents a halogen atom, unsubstituted or substituent-containing alkyl group, unsubstituted or substituent-containing alkoxy group, cyano group, unsubstituted or substituent-containing alkylsulfonyl group, nitro group, or unsubstituted or substituent-containing aryl group, and $n_c$ represents the number of A substituents and is an integer of 0 to 5, and when $n_c$ is 2 or more, the plurality of the A substituents may be the same as, or different from, each other.

Effects of the Invention

The compound containing a pyridine ring according to the present invention can be synthesized in an industrially advantageous manner, and is useful as an intermediate for producing tetrazolyloxime derivatives that exhibit fungicidal activity. Further, the production method of the present invention enables 2-substituted amino-6-halomethylpyridine derivatives to be obtained with high selectivity and in high yield, and enables the production, in an industrially advantageous manner, of tetrazolyloxime derivatives that exhibit excellent antagonistic effects against plant diseases.

EMBODIMENTS OF THE INVENTION

1. Compound Containing a Pyridine Ring that is Ideal as an Agrochemical Intermediate A compound containing a pyridine ring according to the present invention is a compound represented by formula (1).

The compound may be synthesized in the manner described below.

In the case where n=0,

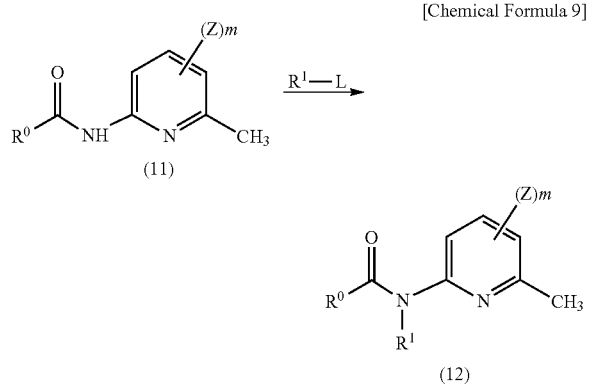

[Chemical Formula 9]

wherein $R^0$, Z and m are the same as defined above, and L represents a leaving group such as a halogen atom.

The compound represented by formula (12) according to the present invention (hereafter referred to as "compound (12)") may be obtained by treating the compound represented by formula (11) (hereafter referred to as "compound (11)") with a compound represented by $R^1$-L. L represents a leaving group such as a halogen atom.

Examples of the compound represented by $R^1$-L include methoxycarbonyl chloride, ethoxycarbonyl chloride, acetyl chloride, benzoyl chloride and p-nitrobenzoyl chloride.

In the case where n=1 to 3,

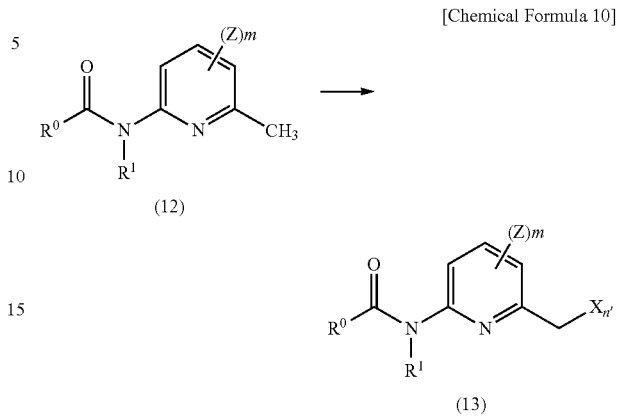

[Chemical Formula 10]

wherein $R^0$, $R^1$, Z, m and X are the same as defined above, and n' represents an integer of 1 to 3.

The compound represented by formula (13) according to the present invention (hereafter referred to as "compound (13)") may be obtained by halogenating the compound (12). The halogenation reaction may be conducted using a conventional method.

In the halogenation reaction, a simple halogen, sulfuryl chloride, phosphorus pentachloride, N-chlorosuccinimide, N-bromosuccinimide, 1,3-dibromo-5,5-dimethylhydantoin, anhydrous copper chloride, aluminum chloride, or the like may be used.

$R^0$ in the compound (I) according to the present invention represents a $C_{1-6}$ alkoxy group, $C_{1-6}$ alkoxy-$C_{1-6}$ alkoxy group, $C_{1-6}$ alkoxy-$C_{1-6}$ alkyl group, 1,3-dioxane-2-yl-$C_{1-6}$ alkyl group, or $CR^{01}C(=NOR^{02})$ group (wherein each of $R^{01}$ and $R^{02}$ independently represents a $C_{1-6}$ alkyl group).

Examples of the $C_{1-6}$ alkoxy group for $R^0$ include a methoxy group, ethoxy group, n-propoxy group, i-propoxy group, n-butoxy group, i-butoxy group, s-butoxy group, t-butoxy group, n-pentyloxy group and n-hexyloxy group.

Examples of the $C_{1-6}$ alkoxy-$C_{1-6}$ alkoxy group for $R^0$ include a methoxymethoxy group, ethoxymethoxy group, methoxyethoxy group, 3-ethoxypropoxy group, 2-ethoxybutoxy group, 4-butoxybutoxy group, 1-butoxypentoxy group, 3-isopropoxy-2-methylpropoxy group and 1-methoxy-2-ethoxyethoxy group.

Examples of the $C_{1-6}$ alkoxy-$C_{1-6}$ alkyl group for $R^0$ include a methoxymethyl group, ethoxymethyl group, methoxyethyl group, methoxypropyl group, ethoxybutyl group, methoxybutyl group, methoxyhexyl group, propoxyoctyl group, 2-methoxy-1,1-dimethylethyl group, 1-ethoxy-1-methylethyl group and 1-ethoxy-2-methoxyethyl group.

Examples of the 1,3-dioxane-2-yl-$C_{1-6}$ alkyl group for $R^0$ include a 1,3-dioxane-2-yl-methyl group and 1,3-dioxane-2-yl-ethyl group.

Each of $R^{01}$ and $R^{02}$ in the $CR^{01}C(=NOR^{02})$ group for $R^0$ independently represents a $C_{1-6}$ alkyl group such as a methyl group, ethyl group, n-propyl group, i-propyl group, n-butyl group or n-hexyl group.

Specific examples of the $CR^{01}C(=NOR^{02})$ group for $R^0$ include $CH_3C(=NOCH_3)$, $CH_3C(=NOC_3H)$ and $C_2H_5C(=NOCH_3)$.

$R^1$ in the compound (I), the compound (12) and the compound (13) according to the present invention represents a $C_{1-2}$ alkoxycarbonyl group, an acetyl group, or a benzoyl group that may be substituted with a nitro group.

Examples of the $C_{1-2}$ alkoxycarbonyl group for $R^1$ include a methoxycarbonyl group and an ethoxycarbonyl group.

Examples of the benzoyl group that may be substituted with a nitro group for $R^1$ include a p-nitrobenzoyl group.

Further, Z and m in formula (1), formula (12) and formula (13) are the same as Z and m described below for formula (7).

X in formula (1) represents a halogen atom, and examples of the halogen atom include a fluorine atom, chlorine atom, bromine atom and iodine atom. Of these, a chlorine atom or a bromine atom is preferred, and a bromine atom is particularly desirable.

The compound (1) according to the present invention is useful as an intermediate for producing a tetrazolyloxime derivative that exhibits fungicidal activity.

2. Production method that enables a 2-substituted amino-6-halomethylpyridine derivative, Which is Useful as a Synthetic Intermediate for Agrochemicals and the Like, to be Obtained In High Yield A method for producing a halogenated picoline derivative according to the present invention includes a step B1 of reacting a compound represented by formula (2) and a halogenating agent within an organic solvent, and a step B2 of reducing the reaction product obtained in the step B1.

[Step B1]

The raw material used in the production method of the present invention is a compound represented by formula (2).

$R^{1b}$ in formula (2) represents an unsubstituted or substituent-containing alkoxycarbonyl group. There are no particular limitations on the substituent, provided it is inactive in the halogenation reaction. The alkoxy group within the alkoxycarbonyl group preferably contains 1 to 6 carbon atoms.

Specific examples of the unsubstituted alkoxycarbonyl group for $R^{1b}$ include a methoxycarbonyl group, ethoxycarbonyl group, i-propoxycarbonyl group, n-propoxycarbonyl group, n-butoxycarbonyl group, i-butoxycarbonyl group, s-butoxycarbonyl group and t-butoxycarbonyl group.

Examples of the substituent-containing alkoxycarbonyl group for $R^{1b}$ include a cyanomethoxycarbonyl group, 1-cyanoethoxycarbonyl group, 2-cyanoethoxycarbonyl group, nitromethoxycarbonyl group, chloromethoxycarbonyl group, fluoromethoxycarbonyl group, difluoromethoxycarbonyl group, trifluoromethoxycarbonyl group, 2-fluoroethoxycarbonyl group, 2,2,2-trifluoroethoxycarbonyl group, methoxymethoxycarbonyl group, ethoxymethoxycarbonyl group, 1-methoxyethoxycarbonyl group, 2-methoxyethoxycarbonyl group and 2-chloroethoxymethoxycarbonyl group.

Among these, $R^{1b}$ is preferably an unsubstituted alkoxycarbonyl group, more preferably an unsubstituted alkoxycarbonyl group in which the alkoxy group contains 1 to 6 carbon atoms, and most preferably a t-butoxycarbonyl group.

$R^{2b}$ in formula (2) represents an unsubstituted or substituent-containing alkoxycarbonyl group, unsubstituted or substituent-containing acyl group, unsubstituted or substituent-containing aryloxycarbonyl group, or unsubstituted or substituent-containing heterocyclic oxycarbonyl group.

Examples of the unsubstituted alkoxycarbonyl group for $R^{2b}$ include a methoxycarbonyl group, ethoxycarbonyl group, i-propoxycarbonyl group, n-propoxycarbonyl group, n-butoxycarbonyl group, i-butoxycarbonyl group, s-butoxycarbonyl group and t-butoxycarbonyl group.

Examples of the substituent-containing alkoxycarbonyl group for $R^{2b}$ include a cyanomethoxycarbonyl group, 1-cyanoethoxycarbonyl group, 2-cyanoethoxycarbonyl group, nitromethoxycarbonyl group, chloromethoxycarbonyl group, fluoromethoxycarbonyl group, difluoromethoxycarbonyl group, trifluoromethoxycarbonyl group, 2-fluoroethoxycarbonyl group, 2,2,2-trifluoroethoxycarbonyl group, methoxymethoxycarbonyl group, ethoxymethoxycarbonyl group, 1-methoxyethoxycarbonyl group, 2-methoxyethoxycarbonyl group and 2-chloroethoxymethoxycarbonyl group.

The acyl group for $R^{2b}$ is a group in which a hydrogen atom, or an alkyl group, alkenyl group, alkynyl group, aryl group or heterocyclic group, is bonded to a carbonyl group.

Examples of the unsubstituted acyl group include a formyl group; alkylcarbonyl groups such as an acetyl group, propionyl group, n-propylcarbonyl group, n-butylcarbonyl group, octanoyl group, i-propylcarbonyl group, i-butylcarbonyl group, pivaloyl group and isovaleryl group; alkenylcarbonyl groups such as an acryloyl group and methacryloyl group; alkynylcarbonyl groups such as a propioloyl group; arylcarbonyl groups such as a benzoyl group; and heterocyclic carbonyl groups such as a 2-pyridylcarbonyl group and thienylcarbonyl group.

Examples of the substituent-containing acyl group for $R^{2b}$ include a fluoroacetyl group, chloroacetyl group, nitroacetyl group, cyanoacetyl group, methoxyacetyl group, dibromoacetyl group, trifluoroacetyl group, trichloroacetyl group, tribromoacetyl group, 3,3,3-trifluoropropionyl group, 3,3,3-trichloropropionyl group, 2,2,3,3,3-pentafluoropropionyl group and 4-chlorobenzoyl group.

Examples of the unsubstituted aryloxycarbonyl group for $R^{2b}$ include a phenyloxycarbonyl group, 1-naphthyloxycarbonyl group, 2-naphthyloxycarbonyl group, azulenyloxycarbonyl group, indenyloxycarbonyl group, indanyloxycarbonyl group and tetralinyloxycarbonyl group.

Examples of the substituent-containing aryloxycarbonyl group for $R^{2b}$ include a 6-methylphenyloxycarbonyl group, 4-methylphenyloxycarbonyl group, 4-fluorophenyloxycarbonyl group, 4-chlorophenyloxycarbonyl group, 2,4-dichlorophenyloxycarbonyl group, 3,4-dichlorophenyloxycarbonyl group, 3,5-dichlorophenyloxycarbonyl group, 2,6-difluorophenyloxycarbonyl group, 4-trifluoromethylphenyloxycarbonyl group, 4-methoxyphenyloxycarbonyl group, 3,4-dimethoxyphenyloxycarbonyl group, 3,4-methylenedioxyphenyloxycarbonyl group, 3-phenoxyphenyloxycarbonyl group, 4-trifluoromethoxyphenyloxycarbonyl group and 4-methoxy-1-naphthyloxycarbonyl group.

Examples of the unsubstituted heterocyclic oxycarbonyl group for $R^{2b}$ include unsaturated heterocyclic 5-membererd ring oxycarbonyl groups such as a furan-2-yloxycarbonyl group, furan-3-yloxycarbonyl group, thiophen-2-yloxycarbonyl group, thiophen-3-yloxycarbonyl group, pyrrol-2-yloxycarbonyl group, pyrrol-3-yloxycarbonyl group, oxazol-2-yloxycarbonyl group, oxazol-4-yloxycarbonyl group, oxazol-5-yloxycarbonyl group, thiazol-2-yloxycarbonyl group, thiazol-4-yloxycarbonyl group, thiazol-5-yloxycarbonyl group, isooxazol-3-yloxycarbonyl group, isooxazol-4-yloxycarbonyl group, isooxazol-5-yloxycarbonyl group, isothiazol-3-yloxycarbonyl group, isothiazol-4-yloxycarbonyl group, isothiazol-5-yloxycarbonyl group, imidazol-2-yloxycarbonyl group, imidazol-4-yloxycarbonyl group, imidazol-5-yloxycarbonyl group, pyrazol-3-yloxycarbonyl group, pyrazol-4-yloxycarbonyl group, pyrazol-5-yloxycarbonyl group, 1,3,4-oxadiazol-2-yloxycarbonyl group, 1,3,4-thiadiazol-2-yloxycarbonyl group, 1,2,3-triazol-4-yloxycarbonyl group, 1,2,4-triazol-3-yloxycarbonyl group and 1,2,4-triazol-5-yloxycarbonyl group; unsaturated heterocyclic 6-membererd ring oxycarbonyl groups such as a pyridin-2-yloxycarbonyl group, pyridin-3-yloxycarbonyl group, pyridin-4-yloxycarbonyl group, 5-chloro-3-pyridyloxycarbonyl group, 3-trifluoromethyl-2-pyridyloxycarbonyl group, pyridazin-3-yloxycarbonyl group, pyridazin-4-yloxycarbonyl group, pyrazin-2-yloxycarbonyl group, pyrimidin-5-yloxycarbonyl group, 1,3,5-triazin-2-yloxycarbonyl group and 1,2,4-triazin-3-yloxycarbonyl group; and saturated or partially unsaturated heterocyclic oxycarbonyl groups such as a tetrahydrofuran-2-yloxycarbonyl group, tetrahydropyran-4-yloxycarbonyl group, piperidin-3-yloxycarbonyl group, pyrrolidin-2-yloxycarbonyl group, morpholino-oxycarbonyl group, piperidino-oxycarbonyl group, piperazino-oxycarbonyl group, N-methylpiperazino-oxycarbonyl group, aziridino-oxycarbonyl group, azetidino-oxycarbonyl group, pyrrolidino-oxycarbonyl group and oxazolin-2-yloxycarbonyl group.

Examples of the substituent-containing heterocyclic oxycarbonyl group for $R^{2b}$ include a 3-trifluoromethylpyridin-2-yloxycarbonyl group, 4-trifluoromethoxy-2-pyridyloxycarbonyl group, 3-methyl-1-pyrazolyloxycarbonyl group, 4-trifluoromethyl-1-imidazolyloxycarbonyl group and 3,4-difluoropyrrolidino-oxycarbonyl group.

Among these groups, $R^{2b}$ in formula (2) is preferably an unsubstituted or substituent-containing benzoyl group. There are no particular limitations on the substituent on the benzoyl group, provided it is inactive in the halogenation reaction.

Specific examples of the substituent-containing benzoyl group for $R^{2b}$ include a 2,6-dimethoxybenzoyl group, 3,5-nitrobenzoyl group, 2,4,6-trichlorobenzoyl group and 4-chlorobenzoyl group.

Z and m in formula (2) are the same as Z and m described below for formula (7).

There are no particular limitations on the halogenating agent used in the step B1, and any of the compounds used for performing halogenation in conventional synthesis reactions may be used.

Examples of the halogenating agent include compounds which themselves function as halogenating agents, and compounds which are converted to a halogenating agent within the reaction system. Specific examples of the halogenating agent include bromine ($Br_2$), chlorine ($Cl_2$), hydrogen bromide, hydrogen chloride; metal bromides such as lithium bromide, potassium bromide, sodium bromide, magnesium bromide, calcium bromide, barium bromide, aluminum bromide, phosphorus tribromide and phosphorus pentabromide; ammonium bromides such as ammonium bromide, tetramethylammonium bromide, tetraethylammonium bromide and tetra-n-butylammonium bromide; as well as trimethylsilyl bromide, BrF, $BrF_3$, $BrF_5$, BrCl, $BrCl_3$, bromine-pyridine complex, 1,3-dibromo-5,5-dimethylhydantoin, 1,3-diiodo-5,5-dimethylhydantoin, thionyl bromide, hypochlorites, hypobromites, cyanuric chloride, N-bromosuccinimide (NBS), N-chlorosuccinimide (NCS), N-iodosuccinimide (NIS), dimethyldichlorohydantoin and trichloroisocyanuric acid. Among these, brominating agents are preferred, and dimethyldibromohydantoin is particularly preferred.

Although there are no particular limitations on the amount used of the halogenating agent, the amount of halogen atoms per 1 mol of the compound represented by formula (2) is preferably within a range from 0.1 to 10 mols, and more preferably from 1 to 5 mols.

Examples of the organic solvent used in the step B1 include ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; polar aprotic solvents such as acetone, methyl ethyl ketone, cyclohexanone, acetonitrile, propionitrile, N,N-dimethylformamide, dimethylsulfoxide, hexamethylphosphoric triamide, sulfolane, dimethylacetamide and N-methylpyrrolidone; protic solvents such as acetic acid; and water.

Of these, from the viewpoints of suppressing side reactions, and ensuring selective halogenation of the methyl group in the compound represented by formula (2), benzene or a halogenated hydrocarbon is preferable.

In the present invention, the step B1 is preferably performed in the presence of a base. When a base is present in the reaction system, side reactions are suppressed, and the halogenation of the methyl group in the compound represented by formula (2) proceeds with better selectivity.

Examples of the base include alkali metal hydroxides such as sodium hydroxide and potassium hydroxide; alkaline earth metal hydroxides such as magnesium hydroxide and calcium hydroxide; carbonates such as sodium carbonate, potassium carbonate, magnesium carbonate, calcium carbonate, sodium hydrogen carbonate and potassium hydrogen carbonate; hydrides such as sodium hydride and calcium hydride; metal alkoxides such as sodium methoxide, sodium ethoxide and magnesium methoxide; and organic bases such as triethylamine, diisopropylethylamine, pyridine, N,N-dimethylaminopyridine, 1,4-diazabicyclo[2.2.2]octane, 4-(dimethylamino)pyridine, 1,8-diazabicyclo[5.4.0]undec-7-ene and 1,5-diazabicyclo[4.3.0]non-5-ene. Any one of these bases may be used alone, or a combination of two or more bases may be used. Among the above bases, sodium hydrogen carbonate is preferred.

The amount used of the base is preferably within a range from 0.1 to 10 mols, and more preferably from 0.5 to 2 mols, per 1 mol of the compound represented by formula (2).

There are no particular limitations on the procedure and the like adopted for the reaction between the compound represented by formula (2) and the halogenating agent. For example, the compound represented by formula (2), and where necessary sodium hydrogen carbonate, may be added to the organic solvent, and the halogenating agent then added gradually to the reaction mixture to cause the reaction to proceed. The temperature during the period from the start of the reaction to the completion of the reaction may be either kept at a constant temperature or varied, but is preferably within a range from 0 to 200° C., and more preferably from room temperature to 150° C.

By conducting the step B1, the methyl group within the compound represented by formula (2) is selectively halogenated. As a result, a reaction product containing a monohalogenated picoline derivative represented by formula (3), a dihalogenated picoline derivative represented by formula (14) and/or a trihalogenated picoline derivative represented by formula (15) is obtained. Subjecting the reaction product to purification by conventional methods to isolate the monohalogenated picoline derivative represented by formula (3) in a high degree of purity requires considerable cost and time. Accordingly, in the present invention, the step B2 described below is performed.

[Chemical Formula 11]

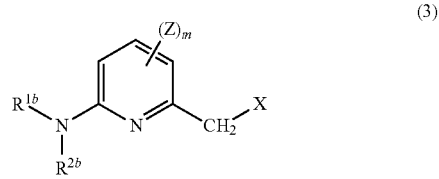

(3)

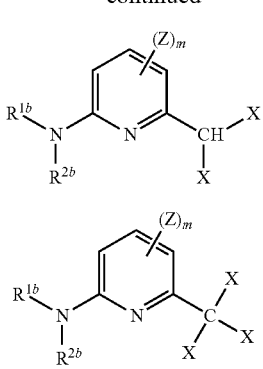

[Step B2]

There are no particular limitations on the method used for reducing the mixed reaction product containing the compounds represented by formula (3), formula (14) and formula (15) obtained in the step B1.

Examples of methods that may be used include a method in which the reaction product obtained in the step B1 is reacted in the presence of an acid and a metal within an organic solvent, and a method in which hydrogen is added to and reacted with the reaction product obtained in the step B1 within an organic solvent.

Examples of the acid used in the above method include inorganic acids such as hydrochloric acid, sulfuric acid and phosphoric acid, and organic acids such as acetic acid, propionic acid and butyric acid.

Examples of the metal used in the above method include zinc, iron, tin, cobalt, nickel and aluminum. The metal is preferably in the form of a fine powder.

There are no particular limitations on the amounts used of the acid and the metal, provided they are sufficient to generate the amount of hydrogen required to effect the reduction reaction. The required amount of hydrogen is preferably within a range from 0.6 to 1.5 mols per 1 mol of the halogenated picoline derivative represented by formula (14), and is preferably within a range from 1.2 to 3.0 mols per 1 mol of the halogenated picoline derivative represented by formula (15).

The reduction reaction is typically conducted at a temperature within a range from −20° C. to reflux temperature, and preferably at a temperature from 20 to 40° C.

In those cases where the reduction is performed on a reaction product in which X represents a bromine atom, which is obtained by using a brominating agent as the halogenating agent in the step B1, a method that includes reacting the reaction product obtained in the step B1, namely the brominated picoline derivative represented by formula (4) and/or the brominated picoline derivative represented by formula (5), with a phosphite ester and a base within an organic solvent is particularly desirable.

The phosphite ester used in the above method is represented by $P(OR)_3$, wherein the oxidation number of phosphorus is +3. R represents a hydrogen atom, an alkyl group, an aryl group or the like, and at least one of the three R groups is a group other than a hydrogen atom.

Examples of the phosphite ester include triphenyl phosphite, tris(nonylphenyl) phosphite, tris(2,4-di-tert-butylphenyl)phosphite, trinonyl phosphite, tridecyl phosphite, trioctyl phosphite, trioctadecyl phosphite, distearylpentaerythritol diphosphite, tricyclohexyl phosphite, monobutyldiphenyl phosphite, monooctyldiphenyl phosphite, distearylpentaerythritol diphosphite, bis(2,4-di-tert-butylphenyl)pentaerythritol phosphite, bis(2,6-di-tert-butyl-4-methylphenyl)pentaerythritol phosphite, 2,2-methylene-bis(4,6-di-tert-butylphenyl)octyl phosphite, dimethyl phosphite, diethyl phosphite, trimethyl phosphite and triethyl phosphite.

The amount used of the phosphite ester is preferably within a range from 0.1 to 20 mols per 1 mol of the brominated picoline derivative represented by formula (4), and is preferably within a range from 0.2 to 40 mols per 1 mol of the brominated picoline derivative represented by formula (5).

Examples of the base used in the above method include alkali metal hydroxides such as sodium hydroxide and potassium hydroxide; alkaline earth metal hydroxides such as magnesium hydroxide and calcium hydroxide; carbonates such as sodium carbonate, potassium carbonate, magnesium carbonate and calcium carbonate; hydrides such as sodium hydride and calcium hydride; metal alkoxides such as sodium methoxide, sodium ethoxide and magnesium methoxide; and organic bases such as triethylamine, diisopropylethylamine, pyridine, N,N-dimethylaminopyridine, 1,4-diazabicyclo[2.2.2]octane, 4-(dimethylamino)pyridine, 1,8-diazabicyclo[5.4.0]undec-7-ene and 1,5-diazabicyclo[4.3.0]non-5-ene.

The amount used of the base is preferably within a range from 0.1 to 10 mols per 1 mol of the brominated picoline derivative represented by formula (4), and is preferably within a range from 0.2 to 20 mols per 1 mol of the brominated picoline derivative represented by formula (5).

There are no particular limitations on the procedure and the like adopted for the reaction between the reaction product obtained in the step B1, the phosphite ester and the base. For example, the reaction may be conducted by gradually adding the phosphite ester, the base, and where necessary a phase transfer catalyst, to an organic solvent solution containing the reaction product obtained in the step B1. The temperature during the period from the start of the reaction to the completion of the reaction may be either kept at a constant temperature or varied, but is preferably within a range from −70° C. to +100° C., and more preferably from −10° C. to +50° C.

There are no particular limitations on the organic solvent used in the step B2, and examples thereof include the same organic solvents available in the step B1. The reaction product need not necessarily be recovered from the reaction solution obtained in the step B1, and the reaction solution may simply be used, as is, within the step B2.

In the present invention, the step B2 is preferably performed in the presence of a phase transfer catalyst.

Examples of the phase transfer catalyst include quaternary ammonium salts; quaternary phosphonium salts such as tetrabutylphosphonium chloride, tetrabutylphosphonium bromide, benzyltrimethylphosphonium chloride and benzyltrimethylphosphonium bromide; and macrocyclic polyethers such as 12-crown-4, 18-crown-6 and benzo-18-crown-6. Among these, the quaternary ammonium salts are preferred.

Examples of the quaternary ammonium salts include chlorides such as tetramethylammonium chloride, tetraethylammonium chloride, tetra-n-propylammonium chloride, benzyltrimethylammonium chloride, benzyltriethylammonium chloride and benzyltripropylammonium chloride; bromides such as tetramethylammonium bromide, tetraethylammonium bromide, tetra-n-propylammonium bromide, tetrabutylammonium bromide, benzyltrimethylammonium bromide, benzyltriethylammonium bromide and benzyltripropylammonium bromide; and iodides such as tetramethylammonium iodide, tetraethylammonium iodide, tetra-n-propylammonium iodide, benzyltrimethylammonium iodide, benzyltriethylammonium iodide and benzyltripropylammonium iodide. Among these, tetrabutylammonium bromide is preferred.

The amount used of the phase transfer catalyst is preferably within a range from 0.001 to 10 mols, and more preferably from 0.01 to 1 mol, per 1 mol of the compound represented by formula (2). By using the phase transfer catalyst in an amount that satisfies the range, the target product can be obtained in good yield.

By conducting the step B2, the dihalogenated picoline derivative represented by formula (14) and/or the trihalogenated picoline derivative represented by formula (15) are converted to the monohalogenated picoline derivative represented by formula (3). As a result, the content ratio of the monohalogenated picoline derivative represented by formula (3) within the reaction system is increased, and isolation thereof becomes easy.

Following completion of each of the reactions in the above steps B1 and B2, typical post-processing operations may be performed. The targeted monohalogenated picoline derivative represented by formula (3) can then be isolated. Further, if further purification of the product is necessary, then conventional purification methods such as distillation, extraction, recrystallization or column chromatography may be employed.

The structure of the target product may be identified and confirmed by measuring the $^1$H-NMR spectrum, IR spectrum and mass spectrum, and by elemental analysis and the like.

The halogenated picoline derivative obtained using the production method of the present invention is useful as a production intermediate for the active ingredients of agrochemical formulations that assist the growth of agricultural and horticultural crops, as a production intermediate for the active ingredients of antifouling agents that prevent the adhesion of crustaceans and shellfish, as a production intermediate for the active ingredients of fungicides, and as a production intermediate for the active ingredients of antibacterial and moldproofing reagents for walls and bathrooms, or shoes and clothing. By employing the production intermediate, the active ingredients of agrochemical formulations, fungicides, and antibacterial and moldproofing reagents can be produced inexpensively and efficiently.

3. Industrially Advantageous Method for Producing a Tetrazolyloxime Derivative that Exhibits a Superior Antagonistic Effect Against Plant Diseases A tetrazolyloxime derivative represented by formula (9) according to the present invention is a novel compound and is useful as a production intermediate for a tetrazolyloxime derivative represented by formula (10).

A method for producing the tetrazolyloxime derivative represented by formula (9) includes a step C1 of reacting the halogenated picoline derivative represented by formula (7) with a tetrazolylhydroxyimino derivative represented by formula (8).

Further, a method for producing the tetrazolyloxime derivative represented by formula (10) includes the above step C1, and a step C2 of treating the reaction product obtained in the step C1 with a base.

[Step C1]

The raw material used in the production method according to the present invention is the halogenated picoline derivative represented by formula (7).

$R^{1C}$ in formula (7) represents an unsubstituted or substituent-containing alkyl group, or an unsubstituted or substituent-containing alkoxy group. There are no particular limitations on the substituent in $R^{1C}$, provided it is inactive in the reaction with the tetrazolylhydroxyimino derivative represented by formula (8).

The alkyl group for $R^{1C}$ may be a linear, branched or cyclic group. Further, the alkyl group preferably contains 1 to 6 carbon atoms.

Examples of the unsubstituted alkyl group include a methyl group, ethyl group, n-propyl group, i-propyl group, n-butyl group, i-butyl group, s-butyl group, t-butyl group, n-pentyl group, n-octyl group, cyclopropyl group, cyclobutyl group, cyclopentyl group, cyclohexyl group, cycloheptyl group, 2,2-dimethylcyclopropyl group and menthyl group.

Examples of the substituent-containing alkyl group include a chloromethyl group, fluoromethyl group, trifluoromethyl group, methoxymethyl group, ethoxymethyl group, methoxyethyl group, methoxypropyl group, ethoxybutyl group, methoxybutyl group, methoxyhexyl group, propoxyoctyl group, 2-methoxy-1,1-dimethylethyl group, 1-ethoxy-1-methylethyl group, carbomethoxymethyl group, 1-carboethoxy-2,2-dimethyl-3-cyclopropyl group, hydroxymethyl group, hydroxyethyl group and 1-hydroxypropyl group. The substituent-containing alkyl group is preferably a haloalkyl group.

The alkoxy group for $R^{1C}$ may be a linear, branched or cyclic group. Further, the alkoxy group preferably contains 1 to 6 carbon atoms.

Examples of the unsubstituted alkoxy group include a methoxy group, ethoxy group, n-propoxy group, i-propoxy group, n-butoxy group, i-butoxy group, s-butoxy group, t-butoxy group, n-pentyloxy group, n-hexyloxy group, n-decyloxy group, cyclopropyloxy group, cyclobutyloxy group, cyclopentyloxy group, cyclohexyloxy group and menthyloxy group.

Examples of the substituent-containing alkoxy group include a chloromethoxy group, fluoromethoxy group, trifluoromethoxy group, methoxymethoxy group, ethoxymethoxy group, methoxyethoxy group, 3-ethoxypropoxy group, 2-ethoxybutoxy group, 4-butoxybutoxy group, 1-butoxypentoxy group, fluoromethoxymethoxy group, dichloromethoxymethoxy group, 1,2-dibromo-3-methoxypropoxy group and 3-isopropoxy-2-methylpropoxy group.

$R^{2C}$ in formula (7) represents an unsubstituted or substituent-containing alkoxycarbonyl group, or an unsubstituted or substituent-containing acyl group, and specific examples thereof include the same groups as those described above for $R^{2b}$.

Among the groups, $R^{2C}$ in formula (7) is preferably an unsubstituted or substituent-containing benzoyl group.

Examples of the substituent-containing benzoyl group include a 2,6-dimethoxybenzoyl group, 3,5-nitrobenzoyl group, 2,4,6-trichlorobenzoyl group and 4-chlorobenzoyl group.

X in formula (7) represents a halogen atom. Examples of the halogen atom include a fluorine atom, chlorine atom, bromine atom and iodine atom. Of these, a chlorine atom or a bromine atom is preferred.

Z in formula (7) represents a halogen atom, cyano group, nitro group, hydroxyl group, thiol group, formyl group, carboxyl group, unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, unsubstituted or substituent-containing heterocyclic group, $OR^3$, $S(O)_pR^3$, $COR^3$ or $CO_2R^3$.

Examples of the halogen atom for Z include the same atoms as those described above for the halogen atom for X.

The unsubstituted amino group for Z is a group having a structure represented by —$NH_2$. Examples of the substituent-containing amino group include a methylamino group, dimethylamino group, methylethylamino group, diethylamino group, t-butoxycarbonylmethylamino group, t-butoxycarbonylamino group, acetylmethylamino group, acetylethylamino group and benzoylmethylamino group.

Examples of the unsubstituted or substituent-containing alkyl group for Z include the same groups as those described above for the unsubstituted or substituent-containing alkyl group for $R^{1C}$.

The unsubstituted or substituent-containing alkenyl group for Z preferably contains 2 to 8 carbon atoms.

Examples of the unsubstituted alkenyl group include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Examples of the substituent-containing alkenyl group include a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group and 2-methoxyethenyl group.

The unsubstituted or substituent-containing alkynyl group for Z preferably contains 2 to 8 carbon atoms.

Examples of the unsubstituted alkynyl group include an ethynyl group, 1-propynyl group, 2-propynyl group, 1-butynyl group, 2-butynyl group, 3-butynyl group, 1-methyl-2-propynl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Examples of the substituent-containing alkynyl group include a 2-chloroethynyl group, 2-fluoroethynyl group, 3-fluoro-1-propynyl group, 3,3,3-trifluoro-1-propynyl group, 3-fluoro-2-propynyl group and 3-iodo-2-propynyl group.

The unsubstituted or substituent-containing aryl group for Z is a monocyclic or polycyclic aryl group. In the polycyclic aryl group, provided at least one ring is an aromatic ring, the remaining ring(s) may each be a saturated alicyclic ring, an unsaturated alicyclic ring or an aromatic ring.

Examples of the unsubstituted aryl group include a phenyl group, 1-naphthyl group, 2-naphthyl group, azulenyl group, indenyl group, indanyl group and tetralinyl group.

Examples of the substituent-containing aryl group include a 6-methylphenyl group, 4-methylphenyl group, 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 3-phenoxyphenyl group, 4-trifluoromethoxyphenyl group and 4-methoxy-1-naphthyl group.

Examples of the unsubstituted heterocyclic group for Z include unsaturated heterocyclic 5-membererd ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isooxazol-3-yl group, isooxazol-4-yl group, isooxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group and 1,2,4-triazol-5-yl group; unsaturated heterocyclic 6-membererd ring groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group and 1,2,4-triazin-3-yl group; and saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, aziridino group, azetidino group, pyrrolidino group and oxazolin-2-yl group.

Examples of the substituent-containing heterocyclic group include a 3-trifluoromethylpyridin-2-yl group, 4-trifluoromethoxy-2-pyridyl group, 3-methyl-1-pyrazolyl group, 4-trifluoromethyl-1-imidazolyl group and 3,4-difluoropyrrolidino group.

The $R^3$ in the $OR^3$, $S(O)_pR^3$, $COR^3$ and $CO_2R^3$ groups for Z represents an unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, or unsubstituted or substituent-containing heterocyclic group. Further, p represents the number of oxygen atoms within the parentheses, and is an integer of 0 to 2.

Examples of the unsubstituted or substituent-containing amino group, unsubstituted or substituent-containing alkyl group, unsubstituted or substituent-containing alkenyl group, unsubstituted or substituent-containing alkynyl group, unsubstituted or substituent-containing aryl group, and unsubstituted or substituent-containing heterocyclic group for $R^3$ include the same groups as those described above for $R^{1C}$ and Z.

Specific examples of $OR^3$ include a methoxy group, ethoxy group, n-propoxy group, i-propoxy group, n-butoxy group, s-butoxy group, i-butoxy group, t-butoxy group, methoxymethoxy group, ethoxymethoxy group, methoxyethoxy group, ethoxyethoxy group, vinyloxy group, 1-propenyloxy group, 2-propenyloxy group, ethynyloxy group, 1-propynyloxy group, 2-propynyloxy group, aminooxy group, methylaminooxy group, diethylaminooxy group, methoxycarbonylaminooxy group, phenoxy group, trichloromethoxy group, trifluoromethoxy group, difluoromethoxy group, 2,2,2-trifluoroethoxy group, pentafluoroethoxy group and 2-fluoroethoxy group.

Specific examples of $S(O)_pR^3$ include a dimethylaminothio group, chloromethylthio group, 3-butenylthio group, ethynylthio group, 3-methylphenylthio group, methylsulfinyl group, ethylsulfinyl group, 1-butenylsulfinyl group, 1-hexynylsulfinyl group, 2,3-dimethylphenylsulfinyl group, methylsulfonyl group, dimethylaminosulfonyl group, N-ethyl-N-methylaminosulfonyl group, n-hexylsulfonyl group, 2-methyl-2-butenylsulfonyl group, 2-propynylsulfonyl group, 2-naphthylsulfonyl group, phenylsulfonyl group, 2-nitrophenylsulfonyl group and p-tolylsulfonyl group.

Specific examples of $COR^3$ include an acetyl group, benzoyl group, propanoyl group, 1-propylcarbonyl group, t-butylcarbonyl group, cyclopropylcarbonyl group, cyclobutylcarbonyl group, cyclopentylcarbonyl group, vinylcarbonyl group, 1-propenylcarbonyl group, 2-propenylcarbonyl group, i-propenylcarbonyl group, 1-propynylcarbonyl group, 2-propynylcarbonyl group, 3-butenylcarbonyl group, methylaminocarbonyl group, dimethylaminocarbonyl group, N-methyl-N-ethylaminocarbonyl group, aziridinocarbonyl group, azetidinocarbonyl group, pyrrolidinocarbonyl group, piperidiniocarbonyl group, morpholinocarbonyl group, piperazinocarbonyl group and N-methylpiperazinocarbonyl group.

Specific examples of $CO_2R^3$ include a methoxycarbonyl group, trifluoromethoxycarbonyl group, 1-pentenyloxycarbonyl group, 2-propynyloxycarbonyl group and phenoxycarbonyl group.

Among the above groups, Z in formula (7) is preferably a halogen atom, an unsubstituted or substituent-containing amino group, an unsubstituted alkyl group, $OR^3$ or $SR^3$, and is more preferably an unsubstituted or substituent-containing amino group, an unsubstituted alkyl group, $OR^3$ or $SR^3$. The unsubstituted or substituent-containing amino group for Z is preferably an unsubstituted amino group or a dialkylamino group, the unsubstituted alkyl group preferably contains 1 to 4 carbon atoms, $OR^3$ is preferably an alkoxy group containing 1 to 4 carbon atoms, and $SR^3$ is preferably an alkylthio group containing 1 to 4 carbon atoms.

The value of m in formula (7) indicates the number of Z substituents, and is an integer of 0 to 3. When m is 2 or more, the plurality of Z substituents may be the same as, or different from, each other. It is particularly preferable that m be 0.

The halogenated picoline derivative represented by formula (7) may be obtained, for example, by reacting the 2-substituted amino-6-methylpyridine derivative having a corresponding structure with a halogenating agent.

In the step C1, the substance reacted with the halogenated picoline derivative represented by formula (7) is a tetrazolylhydroxyimino derivative represented by formula (8).

In formula (8), Y represents an unsubstituted or substituent-containing alkyl group. Examples of the unsubstituted or substituent-containing alkyl group for Y include the same groups as those described above for $R^{1C}$. The unsubstituted or substituent-containing alkyl group for Y is preferably an unsubstituted alkyl group, more preferably an unsubstituted alkyl group containing 1 to 6 carbon atoms, and most preferably a methyl group.

In formula (8), A represents a halogen atom, unsubstituted or substituent-containing alkyl group, unsubstituted or substituent-containing alkoxy group, cyano group, unsubstituted or substituent-containing alkylsulfonyl group, nitro group, or unsubstituted or substituent-containing aryl group.

Examples of the halogen atom, unsubstituted or substituent-containing alkyl group, unsubstituted or substituent-containing alkoxy group and unsubstituted or substituent-containing aryl group for A include the same atoms and groups as those described above for $R^{1C}$ and Z. The unsubstituted or substituent-containing alkyl group for A is preferably an unsubstituted alkyl group or haloalkyl group, and is more preferably an unsubstituted alkyl group containing 1 to 6 carbon atoms or a haloalkyl group containing 1 to 6 carbon atoms. The unsubstituted or substituent-containing alkoxy group for A is preferably an unsubstituted alkoxy group or haloalkoxy group, and is more preferably an unsubstituted alkoxy group containing 1 to 6 carbon atoms or a haloalkoxy group containing 1 to 6 carbon atoms.

Examples of the unsubstituted alkylsulfonyl group for A include a methylsulfonyl group, ethylsulfonyl group, n-propylsulfonyl group, i-propylsulfonyl group and t-butylsulfonyl group. Examples of the substituent-containing alkylsulfonyl group include a 2-pyridylmethylsulfonyl group, 3-pyridylmethylsulfonyl group, chloromethylsulfonyl group, cyanomethylsulfonyl group, 1-cyanoethylsulfonyl group, 2-cyanoethylsulfonyl group, nitromethylsulfonyl group, chloromethylsulfonyl group, fluoromethylsulfonyl group, difluoromethylsulfonyl group, trifluoromethylsulfonyl group, 2-fluoroethylsulfonyl group, 2,2,2-trifluoroethylsulfonyl group, methoxymethylsulfonyl group, ethoxymethylsulfonyl group, 1-methoxyethylsulfonyl group, 2-methoxyethylsulfonyl group and 2-chloroethoxymethylsulfonyl group. The unsubstituted or substituent-containing alkylsulfonyl group for A is preferably an unsubstituted alkylsulfonyl group, and more preferably an unsubstituted alkylsulfonyl group containing 1 to 6 carbon atoms.

In formula (8), $n_c$ represents the number of A substituents, and is an integer of 0 to 5. When $n_c$ is 2 or more, the plurality of the A substituents may be the same as, or different from, each other. It is particularly preferable that $n_c$ be 0.

The reaction between the halogenated picoline derivative represented by formula (7) and the tetrazolylhydroxyimino derivative represented by formula (8) in the step C1 is a conventional reaction that involves a coupling between a halogeno group and a hydroxyl group. The reaction may be performed, for example, in accordance with the method disclosed in Japanese Unexamined Patent Application, First Publication No. 2003-137875 or International Patent Publication No. WO 03/016303 pamphlet. The reaction is generally performed in the presence of a base.

Examples of the base used in the reaction include alkali metal hydroxides such as sodium hydroxide and potassium hydroxide; alkaline earth metal hydroxides such as magnesium hydroxide and calcium hydroxide; carbonates such as sodium carbonate, potassium carbonate, magnesium carbonate and calcium carbonate; hydrides such as sodium hydride and calcium hydride; metal alkoxides such as sodium methoxide, sodium ethoxide and magnesium methoxide; and organic bases such as triethylamine, diisopropylethylamine, pyridine, N,N-dimethylaminopyridine, 1,4-diazabicyclo[2.2.2]octane, 4-(dimethylamino)pyridine, 1,8-diazabicyclo[5.4.0]undec-7-ene and 1,5-diazabicyclo[4.3.0]non-5-ene. Any one of these bases may be used alone, or a combination of two or more bases may be used.

The amount used of the base in the step C1 is typically within a range from 0.01 to 100 mols, and preferably from 0.1 to 5 mols, per 1 mol of the tetrazolylhydroxyimino derivative represented by formula (8).

The reaction in the step C1 may be conducted in the presence of a solvent or without using a solvent.

There are no particular limitations on the solvent used, provided it is inactive in the reaction. Examples of the solvent include hydrocarbon-based solvents such as pentane, hexane, heptane, benzene, toluene and xylene; halogen-based solvents such as dichloromethane, chloroform and carbon tetrachloride; nitrile-based solvents such as acetonitrile and propionitrile; ether-based solvents such as diethyl ether, dioxane and tetrahydrofuran; amide-based solvents such as N,N-dimethylformamide, N,N-dimethylacetamide and N-methylpyrrolidone; sulfoxide-based solvents such as dimethylsulfoxide; and mixed solvents of the above solvents.

There are no particular limitations on the procedure and the like adopted for the reaction between the halogenated picoline derivative represented by formula (7) and the tetrazolylhydroxyimino derivative represented by formula (8). For example, the reaction may be performed by adding a base and the tetrazolylhydroxyimino derivative represented by formula (8) to an organic solvent solution containing the halogenated picoline derivative represented by formula (7).

The temperature during the period from the start of the reaction to the completion of the reaction in the step C1 may be either kept at a constant temperature or varied, but is typically within a range from −70° C. to +200° C., and preferably from −20° C. to +100° C. The reaction time varies depending on the reaction scale and the like, but is typically within a range from 30 minutes to 24 hours.

By conducting the step C1, a tetrazolyloxime derivative represented by formula (9) can be obtained in an industrially advantageous manner. The tetrazolyloxime derivative represented by formula (9) is a novel substance, and is very useful as a production intermediate for the tetrazolyloxime derivative represented by formula (10) described below.

In formula (9), $R^{1C}$, $R^{2C}$, Z, m, A, $n_c$ and Y are the same as defined above in formula (7) or formula (8).

[Step C2]

Next, in the step C2, the tetrazolyloxime derivative represented by formula (10) may be obtained by treating the reaction product obtained in the step C1 with a base.

The reaction product obtained in the step C1, namely the tetrazolyloxime derivative represented by formula (9), may be reacted with a base without performing any purification operation of the reaction solution obtained in the step C1, or alternatively, the reaction solution obtained in the step C1 may be subjected to a purification operation to isolate the reaction product, namely the tetrazolyloxime derivative represented by formula (9), which may then be treated with a base. Examples of the purification operation include distillation, recrystallization and column chromatography.

There are no particular limitations on the base used in the step C2, provided it is capable of eliminating the $R^{2C}$ group from the tetrazolyloxime derivative represented by formula (9). Examples of the base include alkali metal hydroxides such as sodium hydroxide and potassium hydroxide; alkaline earth metal hydroxides such as magnesium hydroxide and calcium hydroxide; carbonates such as sodium carbonate, potassium carbonate, magnesium carbonate and calcium carbonate; hydrides such as sodium hydride and calcium hydride; metal alkoxides such as sodium methoxide, sodium ethoxide and magnesium methoxide; and organic bases such as triethylamine, diisopropylethylamine, pyridine, N,N-dimethylaminopyridine, 1,4-diazabicyclo[2.2.2]octane, 4-(dimethylamino)pyridine, 1,8-diazabicyclo[5.4.0]undec-7-ene and 1,5-diazabicyclo[4.3.0]non-5-ene. Any one of the bases may be used alone, or a combination of two or more bases may be used.

The amount used of the base in the step C2 is typically within a range from 0.01 to 100 mols, and preferably from 0.1 to 5 mols, per 1 mol of the tetrazolyloxime derivative represented by formula (9). When the reaction solution obtained in the step C1 is used in the step C2 without removing the base therefrom, the amount of base added in the step C2 may be adjusted taking into account the amount used in the step C1.

The reaction in the step C2 may be conducted in the presence of a solvent or in the absence of a solvent. There are no particular limitations on the solvent used, provided it is inactive in the reaction. Specific examples of the solvent include the same solvents as those described above for the step C1. If the solvent used in the step C2 is the same as the solvent used in the step C1, there is no need to perform a solvent substitution when transitioning from the step C1 to the step C2, which is advantageous in terms of production costs.

There are no particular limitations on the procedure and the like adopted for treating the reaction product obtained in the step C1 with a base. For example, the reaction may be performed by adding a base to an organic solvent solution containing the reaction product obtained in the step C1, namely the tetrazolyloxime derivative represented by formula (9).

The temperature during the period from the start of the reaction to the completion of the reaction in the step C2 may be either kept at a constant temperature or varied, but is typically within a range from 0° C. to the boiling point of the solvent, and is preferably within a range from 10 to 60° C. The reaction time varies depending on the concentration of the base and the reaction scale and the like, but is typically within a range from 5 minutes to 24 hours.

By performing the step C2, the tetrazolyloxime derivative represented by formula (10) can be obtained in an industrially advantageous manner.

In formula (10), $R^{1C}$, Z, m, A, $n_c$ and Y are the same as defined above in formula (7) or formula (8).

Following completion of the reaction of the step C2, typical post-processing operations may be performed. The targeted tetrazolyloxime derivative represented by formula (10) can then be isolated. Further, in those cases where further purification of the product is required, conventional purification methods such as distillation, extraction, recrystallization or column chromatography may be employed.

The structure of the target product may be identified and confirmed by measuring the $^1$H-NMR spectrum, IR spectrum and mass spectrum, and by elemental analysis and the like.

The tetrazolyloxime derivative represented by formula (10) obtained using the production method according to the present invention may be converted to a salt. The salt may be produced in accordance with normal methods, by treating the tetrazolyloxime derivative represented by formula (10) with an acid.

The tetrazolyloxime derivative represented by formula (10) or a salt thereof, obtained using the production method according to the present invention, is ideal as an active ingredient of fungicides or the like. The fungicides may be used, for example, as agrochemical formulations that assist the growth of agricultural and horticultural crops, as antifouling agents that prevent the adhesion of crustaceans and shellfish, and as antibacterial and moldproofing reagents for walls and bathrooms, or shoes and clothing.

EXAMPLES

The present invention is described below in further detail based on a series of examples, but the present invention should not be interpreted as being limited to only these examples.

Example A1

[Chemical Formula 12]

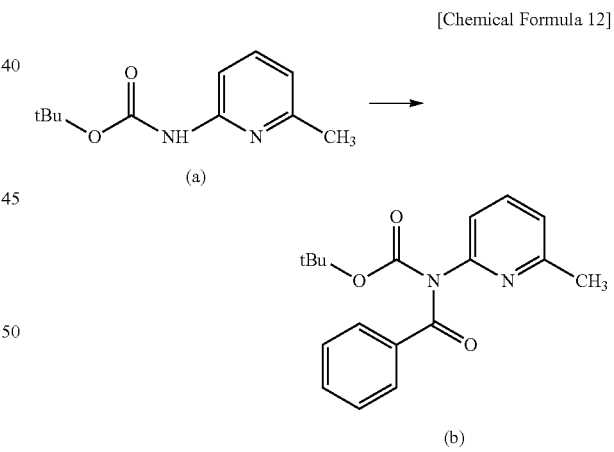

10.52 g (2.5 mmol) of a compound (a) was dissolved in 1.25 ml of toluene (0.5 L/mol). The solution of the compound (a) was then added dropwise, at room temperature, to a liquid prepared by adding 0.13 g of sodium hydride (55%) (1.2 eq.) to a mixture solvent composed of toluene and N,N-dimethylformamide at a ratio of 4/1 (2 L/mol), and the resulting mixture was then aged at room temperature for 30 minutes.

Subsequently, 0.42 g (1.2 eq.) of benzoyl chloride was added dropwise to the reaction mixture under cooling, and the resulting mixture was aged at the temperature for 20 minutes.

The reaction mixture was extracted twice with ethyl acetate (2 L/mol), and the extract was then washed with a saturated saline solution (2 L/mol), dried over anhydrous magnesium sulfate, filtered, and concentrated. The thus obtained crystals were then washed with cooled n-hexane (2 L/mol). A compound represented by formula (b) (hereafter referred to as "compound (b)") was obtained in an amount of 0.66 g. The yield was 84.6%.

Example A2

[Chemical Formula 13]

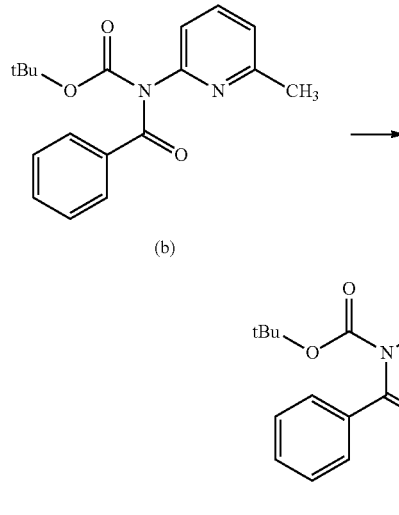

(Bromination)

0.31 g (1 mmol) of the compound (b) was dissolved in 4 ml of chlorobenzene (4 L/mol), and then 0.29 g (1 eq.) of 2,5-di-t-butylhydroquinone and 0.03 g (0.2 eq.) of 2,2'-azobisisobutyronitrile were added sequentially to the resultant solution, followed by stirring at 90° C. for one hour. The resultant liquid was then cooled to room temperature. The resultant liquid was then washed with a 1 N aqueous solution of sodium hydroxide and dried over anhydrous magnesium sulfate, followed by removing the solvent therefrom by distillation under reduced pressure. The residue was purified by silica gel column chromatography (developing solvent: hexane/ethyl acetate=3/1), yielding 0.15 g (yield: 38%) of a compound represented by formula (c).

Using the same procedure as that described for the above production method, a compound represented by formula (1-a) shown in Table 1, a compound represented by formula (1-b) shown in Table 2, and a compound represented by formula (1) shown in Table 3 were obtained. The physical properties and the like of the compounds are shown in Table 1 and Table 2. In the tables, MeOCO represents a methoxycarbonyl group, EtOCO represents an ethoxycarbonyl group, Ac represents an acetyl group, and Bz represents a benzoyl group.

[Chemical Formula 14]

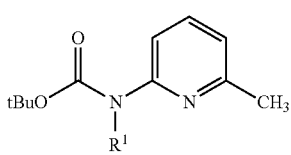

Formula (1-a)

TABLE 1

| Compound number | $R^1$ | Physical properties | NMR |
|---|---|---|---|
| a-1 | MeOCO | m.p. 57.5 to 57.6° C. | |
| a-2 | EtOCO | | $^1$H-NMR (CDCl$_3$) δ ppm: 1.2 (t, 3H), 1.4 (s, 9H), 2.5 (s, 3H), 4.2 (q, 2H), 7.0 (d, 1H), 7.1 (d, 1H), 7.6 (t, 1H) |
| a-3 | Ac | m.p. 77.4 to 77.5° C. | |
| a-4 | Bz | m.p. 93.7 to 93.8° C. | |
| a-5 | p-NO$_2$-Bz | m.p. 114.8 to 114.9° C. | |

[Chemical Formula 15]

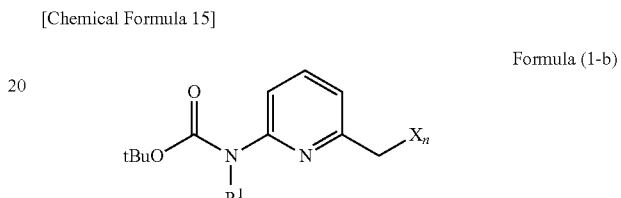

Formula (1-b)

TABLE 2

| Compound number | X | n | $R^1$ | Physical properties | NMR |
|---|---|---|---|---|---|
| a-6 | Br | 1 | MeOCO | m.p. 82.8 to 82.9° C. | |
| a-7 | Br | 1 | EtOCO | m.p. 63.9 to 64.0° C. | |
| a-8 | Br | 1 | Ac | m.p. 98.6 to 100.4° C. | |
| a-9 | Br | 1 | Bz | | $^1$H-NMR (CDCl$_3$) δ ppm: 1.3 (s, 9H), 4.4 (s, 2H), 7.29 (d, 1H), 7.34 (d, 1H), 7.4 (d, 2H), 7.5 (d, 1H), 7.8 (m, 3H) |
| a-10 | Cl | 1 | Bz | | $^1$H-NMR (CDCl$_3$) δ ppm: 1.3 (s, 9H), 4.6 (s, 2H), 7.3 (d, 1H), 7.45 (m, 3H), 7.5 (d, 1H), 7.8 (m, 3H) |
| a-11 | Cl | 1 | p-NO$_2$-Bz | m.p. 89.5 to 89.6° C. | |

[Chemical Formula 16]

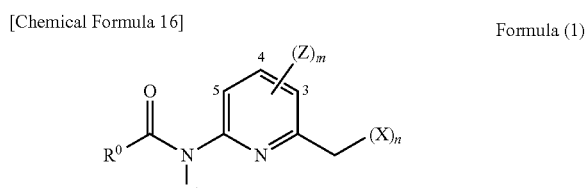

Formula (1)

TABLE 3

| Compound number | $R^0$ | $R^1$ | $(Z)_m$ | $(X)_n$ |
|---|---|---|---|---|
| a-12 | tBuO | MeOCO | H | F |
| a-13 | tBuO | EtOCO | H | Cl |
| a-14 | tBuO | Ac | H | Br$_3$ |
| a-15 | tBuO | Bz | H | I |
| a-16 | tBuO | p-NO$_2$-Bz | H | Br$_2$ |
| a-17 | MeOCH$_2$O | MeOCO | H | H |
| a-18 | EtOC$_2$H$_4$CH(Me)O | Bz | H | H |

TABLE 3-continued

| Compound number | R⁰ | R¹ | (Z)m | (X)n |
|---|---|---|---|---|
| a-19 | iPrOC₃H₆O | Ac | H | H |
| a-20 | (MeO)₂CHCH₂C(Me)₂O | EtOCO | H | H |
| a-21 | MeOC₂H₄CH(EtO)O | Ac | H | H |
| a-22 | MeOCH₂ | Bz | H | Br₂ |
| a-23 | (MeO)₂CH₂ | p-NO₂-Bz | H | Br |
| a-24 | MeC(EtO)₂ | Ac | H | H |
| a-25 | (MeO)₂C₂H₄ | MeOCO | H | H |
| a-26 | EtOCH₂ | EtOCO | H | H |
| a-27 | 1,3-dioxane-2-yl-methyl | MeOCO | H | H |
| a-28 | 1,3-dioxane-2-yl-ethyl | EtOCO | H | F |
| a-29 | 1,3-dioxane-2-yl-propyl | Ac | H | Cl |
| a-30 | 1,3-dioxane-2-yl-buthyl | Bz | H | Br |
| a-31 | 1,3-dioxane-2-yl-penthyl | p-NO₂-Bz | H | I |
| a-32 | MeC=NOMe | MeOCO | H | H |
| a-33 | MeC=NOnPr | EtOCO | H | H |
| a-34 | EtC=NOEt | Ac | H | H |
| a-35 | nPrC=NOMe | Bz | H | H |
| a-36 | iPrC=NOMe | p-NO₂-Bz | H | H |

Example B1

Production of t-butyl benzoyl-(6-methyl-pyridin-2-yl)-carbamate

[Chemical Formula 17]

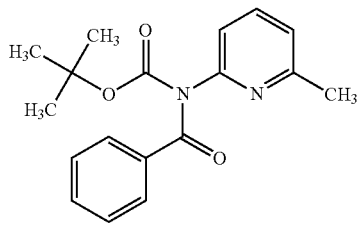

(d)

A reactor that had been flushed with nitrogen was charged with 40 ml of N,N-dimethylformamide, and then 5.23 g of sodium hydride (purity: 55%) and 160 ml of toluene were added to the reactor. A solution containing 20.8 g of t-butyl (6-methyl-pyridin-2-yl)-carbamate in 50 ml of toluene was added dropwise to the suspension in the reactor over a period of 20 minutes and within a temperature range from 20° C. to 25° C. Following completion of the dropwise addition, the mixture was stirred for 30 minutes at a temperature within a range from 20° C. to 25° C. Subsequently, the reaction mixture was cooled to 5° C. or lower, and 13.9 ml of benzoyl chloride was added dropwise over a period of 15 minutes and within a temperature range from 0° C. to 5° C. Following completion of the dropwise addition, the mixture was stirred for 10 minutes at a temperature within a range from 0° C. to 5° C. Subsequently, the reaction mixture was poured into 200 ml of ice water, and the organic layer and the aqueous layer were separated. The aqueous layer was extracted with 20 ml of toluene, and the extract was mixed with the previously separated organic layer. The resultant was washed twice with 50 ml of water, and then washed once with 50 ml of a saturated saline solution. The solvent was removed by distillation under reduced pressure. Hexane was added to the residue, and the mixture was concentrated under reduced pressure. 50 ml of hexane was further added to the residue, and the mixture was heated at 60° C. The mixture was then cooled gradually to 10° C., and stirred for 30 minutes at a temperature of 10° C. or lower. The mixture was then filtered. The solid matter was washed twice with 20 ml of hexane, and then dried by heating, to obtain 29.1 g (93%) of a compound represented by formula (d).

Example B2

Production of t-butyl benzoyl-(6-bromomethyl-pyridin-2-yl)-carbamate

[Chemical Formula 18]

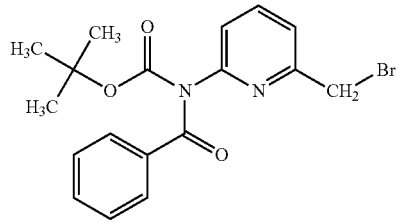

(e)

First, 29.1 g of t-butyl benzoyl-(6-methyl-pyridin-2-yl)-carbamate was dissolved in 372 ml of chlorobenzene. To the resultant solution was added 7.8 g of sodium hydrogen carbonate. The resultant mixture was then heated to 90° C., and then 3.1 g of azobisisobutyronitrile was added thereto, followed by adding 26.6 g of 1,3-dibromo-5,5-dimethylhydantoin in 10 portions over a period of 80 minutes. Following completion of the addition, the mixture was stirred at 90° C. for 30 minutes. The reaction mixture was then cooled to room temperature, washed with 140 ml of 1 N sodium hydroxide, and then washed with a mixed solution composed of 70 ml of water and 23 ml of a saturated saline solution.

The thus obtained organic layer was cooled at 5° C. or lower, and then 14.9 g of a 50% solution of sodium hydroxide, 12.0 ml of diethyl phosphite and 1.5 g of tetrabutylammonium chloride were each added in portions, while the progression of the reaction was confirmed by thin-layer chromatography. Following completion of the additions, the mixture was stirred for 15 minutes at a temperature within a range from 0° C. to 5° C.

The disappearance of the spots corresponding with the dibromo compounds and the tribromo compound and the production of the compound represented by formula (e) (the monobromo compound) were confirmed by performing thin-layer chromatography. The reaction solution was directly used in example B3 without subjecting to any post-processing.

Example B3

Production of t-butyl benzoyl-{6-([Z]-(1-methyl-1H-5-tetrazolyl)phenylmethylene-aminooxymethyl)-2-pyridyl}carbamate

[Chemical Formula 19]

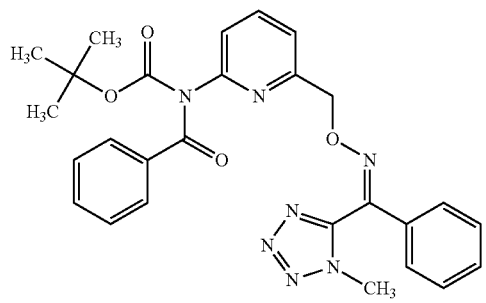

(f)

To the reaction solution obtained in the example B2 was added 37.2 g of a 20% solution of sodium hydroxide, and the resulting mixture was stirred for 30 minutes at a temperature within a range from 20° C. to 25° C. Subsequently, 18.9 g of (1-methyl-1H-5-tetrazolyl)-phenyl-methanone-oxime was added, and the reaction mixture was stirred for 3.5 hours at a temperature within a range from 20° C. to 25° C.

The disappearance of the target substance and the production of a compound represented by formula (f) were confirmed by performing thin-layer chromatography. The reaction solution was directly used in example B4 without subjecting to any post-processing.

Example B4

Production of t-butyl {6-([Z]-(1-methyl-1H-5-tetrazolyl)phenylmethylene-aminooxymethyl)-2-pyridyl}carbamate

[Chemical Formula 20]

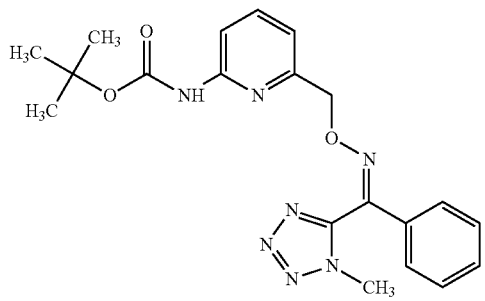

(g)

To the reaction solution obtained in the example B3 was added 37.2 g of a 20% solution of sodium hydroxide, and the resulting mixture was stirred at 40° C. for 15 hours. The disappearance of the raw materials and the production of the target product were confirmed by performing thin-layer chromatography. Subsequently, the reaction mixture was separated into an organic layer and an aqueous layer. The organic layer was washed with 93 ml of 1 N sodium hydroxide. The aqueous layer was extracted with 23 ml of chlorobenzene, and the extract was mixed with the previously separated organic layer, followed by washing the mixture with 47 ml of a saturated saline solution. The solvent was removed by distillation under reduced pressure, and then methanol was added to the residue, followed by concentrating the mixture under reduced pressure. The process of adding methanol and performing concentration under reduced pressure was further repeated twice. Subsequently, 47 ml of methanol was added to the resultant, and the mixture was heated under reflux to obtain a homogenous solution. The solution was then cooled gradually to 10° C., and stirred for 30 minutes at a temperature of 10° C. or lower. The resulting liquid was then filtered. The solid matter was washed twice with 19 ml of methanol, and then dried under heat, yielding 26.6 g of a compound represented by formula (g). The melting point of the solid material was 141.5 to 141.6° C. The through-yield from the t-butyl benzoyl-(6-methyl-pyridin-2-yl)-carbamate (example B2) was 70%.

Example B5

Production of t-butyl acetyl-(6-methyl-pyridin-2-yl)-carbamate

[Chemical Formula 21]

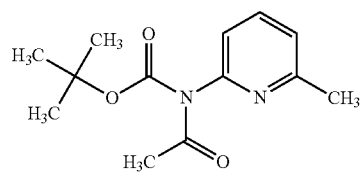

(h)

With the exception of using acetyl chloride instead of benzoyl chloride, the same procedure as the production example B1 was used to produce a compound represented by formula (h). The melting point of the compound was 77.4 to 77.5° C.

Example B6

Production of t-butyl acetyl-(6-bromomethyl-pyridin-2-yl)-carbamate

[Chemical Formula 22]

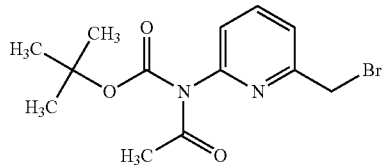

(i)

First, 1.05 g (4.2 mmol) of t-butyl acetyl-(6-methyl-pyridin-2-yl)-carbamate was dissolved in 17 ml of chlorobenzene (4 L/mol). 1.2 g (1 eq.) of 1,3-dibromo-5,5-dimethylhydantoin and 0.14 g (20 mol %) of 2,2'-azobisisobutyronitrile were added to the resulting solution, and the resulting mixture was stirred at 90° C. for one hour. Subsequently, the reaction mixture was cooled, the precipitate was removed by filtration, and the filtrate was concentrated to approximately half volume.

To the thus obtained residue were added, under cooling, 0.58 g of diethyl phosphite and 0.54 g of diisopropylethylamine, and the resulting mixture was stirred at room temperature for 19 hours. The disappearance of the raw materials was confirmed by performing thin-layer chromatography (ethyl acetate:hexane=1:4 (volumetric ratio)), and then the resultant was extracted with chloroform three times. The extract was dried over anhydrous magnesium sulfate and filtered, and the solvent was then removed by distillation under reduced pressure.

Example B7

Production of t-butyl {6-([Z]-(1-methyl-1H-5-tetrazolyl)phenylmethylene-aminooxymethyl)-2-pyridyl}carbamate

[Chemical Formula 23]

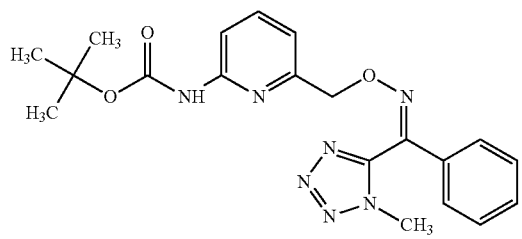

(j)

First, 0.85 g of (1-methyl-1H-5-tetrazolyl)-phenyl-methanone-oxime was dissolved in 6 ml of chlorobenzene (1.5 L/mol). To the resulting solution were added dropwise, at 0° C., 1.75 ml (2 eq.) of a 20% aqueous solution of sodium hydroxide, 0.27 g (20 mol %) of tetrabutylammonium bromide, and a solution prepared by dissolving the residue obtained in the example B6 in 3 ml of chlorobenzene (0.8 L/mol). The resulting mixture was stirred overnight at room temperature. Following confirmation by performing thin-layer chromatography (ethyl acetate:hexane=1:4) that the raw materials had disappeared, the reaction mixture was extracted with chloroform three times. The organic layer was dried over anhydrous magnesium sulfate and filtered, and the solvent was then removed by distillation under reduced pressure. The residue was purified using an automated fraction collector (manufactured by Yamazen Corporation), yielding t-butyl acetyl-{6-([Z]-(1-methyl-1H-5-tetrazolyl)phenylmethylene-aminooxymethyl)-2-pyridyl}carbamate in a yield of 67.4%.

Next, 1.28 g (2.835 mmol) of the thus obtained t-butyl acetyl-{6-([Z]-(1-methyl-1H-5-tetrazolyl)phenylmethylene-aminooxymethyl)-2-pyridyl}carbamate was dissolved in 23 ml of methanol (8 L/mol). To the resulting solution was added 3.51 ml (3 eq.) of a 10% aqueous solution of sodium hydroxide, and the resulting mixture was stirred at room temperature for 15 hours. Subsequently, the reaction liquid was concentrated. The resulting concentrate was washed with water, washed with hexane, and then washed with a small amount of methanol. The product was then air-dried, yielding 0.98 g of the target compound (yield: 84.5%). The through-yield from the t-butyl acetyl-(6-methyl-pyridin-2-yl)-carbamate (example B6) was 73.8%.

Example B8

Production of t-butyl t-butoxycarbonyl-(6-methyl-pyridin-2-yl)-carbamate

[Chemical Formula 24]

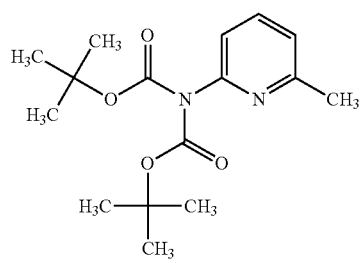

(k)

First, 38 g of 6-methyl-pyridin-2-ylamine, 169 g of bis(t-butoxycarbonyl) oxide, 18 ml (2.48 g) of triethylamine and 18 ml (1.84 g) of pyridine were dissolved in 340 ml of dimethylformamide. The resulting solution was then heated gradually. The liquid temperature was eventually raised to 90° C. while monitoring the state of generated carbon dioxide. The reaction mixture was then held at the temperature for 5 hours. Following confirmation by performing thin-layer chromatography that the raw materials had disappeared, the reaction mixture was poured into a mixed solution containing 500 ml of each of a saturated aqueous solution of ammonium chloride, a saturated aqueous solution of sodium hydrogen carbonate and a saturated aqueous solution of sodium chloride, and the resulting mixture was then extracted with ethyl acetate. The extract was then dried over anhydrous magnesium sulfate, filtered and concentrated. Subsequently, a column purification was performed, yielding 81 g (74.7%) of the target product.

Example B9

Production of 2-bis(t-butoxycarbonyl)amino-6-bromomethyl-pyridine

[Chemical Formula 25]

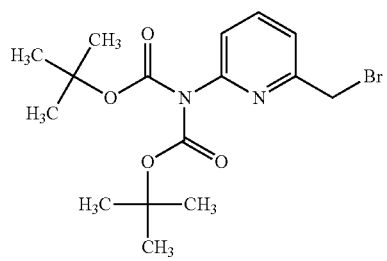

(l)

To 102.8 g (334 mmol) of t-butyl t-butoxycarbonyl-(6-methyl-pyridin-2-yl)-carbamate were added 10.95 g (20 mol %) of 2,2'-azobisisobutyronitrile and 1,330 ml of chlorobenzene. To the resulting mixture was added 95.31 g of 1,3-dibromo-5,5-dimethylhydantoin, and the temperature of the mixture was then raised to 90° C. at a rate of 2° C./minute and held at the temperature for one hour. Subsequently, the reaction mixture was cooled to 20° C., the precipitate was filtered off, and the volume of chlorobenzene was reduced by half by distillation. The thus obtained residue was cooled to 10° C. or lower, and then 46.03 g (43 ml) of diisopropylethylamine and 43.08 g (58 ml) of diethyl phosphite were added thereto, followed by aging the mixture at room temperature for 16.5 hours. Following confirmation by performing thin-layer chromatography that the raw materials had disappeared, the reaction mixture was washed with 300 ml of 3 N hydrochloric acid, and then further washed with 500 ml of a saturated saline solution. The resulting solution was then dried over anhydrous magnesium sulfate and filtered, yielding a solution of 2-bis(t-butoxycarbonyl)amino-6-bromomethyl-pyridine.

Example B10

Production of t-butyl {6-([Z]-(1-methyl-1H—S-tet-razolyl)phenylmethylene-aminooxymethyl)-2-pyridyl}carbamate

[Chemical Formula 26]

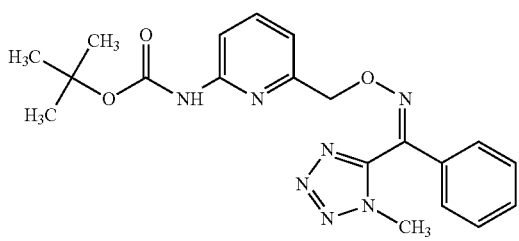

(m)

To the solution of 2-bis(t-butoxycarbonyl)amino-6-bromomethyl-pyridine obtained in the example B9 were added 67.7 g of (1-methyl-1H-5-tetrazolyl)-phenyl-methanone-oxime, 667 ml of a 1 N aqueous solution of sodium hydroxide and 5.4 g (5 mol %) of tetrabutylammonium bromide, and the resulting mixture was aged at room temperature for two hours. Following confirmation by performing thin-layer chromatography that the raw materials had disappeared, 500 ml of water and 500 ml of chloroform were added, and an extraction was performed. The aqueous layer was extracted with 500 ml of chloroform, and then washed with 500 ml of water. The extract was dried over anhydrous magnesium sulfate, filtered and then concentrated. The thus obtained residue was dissolved in 2.5 L of methanol, and 1 L of a 1 N aqueous solution of sodium hydroxide was then added to the solution at room temperature. The reaction was allowed to proceed at room temperature for approximately 20 hours.

The precipitated crystals were collected by filtration. The thus obtained crystals were washed three times with 500 ml of water, and then dried in a desiccators, yielding 98.16 g of the Z-isomer of the target product (purity: 98.5%, yield: 72.6%). On the other hand, 5 L of water was added to the above filtrate, and the mixture was extracted three times with 1,000 ml of ethyl acetate. The ethyl acetate layer was washed with 1 L of water, dried over anhydrous magnesium sulfate, filtered, and then concentrated. The thus obtained residue was purified using a fraction collector manufactured by Biotage AB, yielding 6.1 g of the target product (E:Z isomeric mixture). The total yield was 77.1%.

Example C1

[Chemical Formula 27]

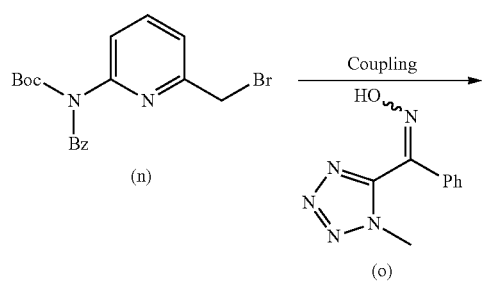

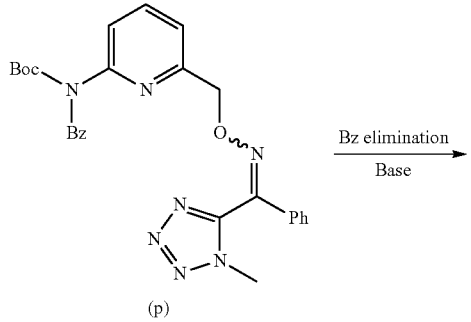

To 54.7 g of a solution prepared by dissolving 5.87 g (15 mmol) of a compound represented by formula (n) in 44 mL of chlorobenzene were added 48.0 g (60 mmol) of an aqueous solution of NaOH having a concentration of 5% by weight, 0.24 g (0.75 mmol) of tetrabutylammonium bromide, and 3.77 g (purity: 97.0% by weight, 18 mmol) of a compound represented by formula (o).

The resulting mixture was stirred at room temperature for 4 hours, and the disappearance of the compound represented by formula (n) and the production of a compound represented by formula (p) were confirmed by high-performance liquid chromatography.

The reaction mixture was heated to 40° C., and 4.29 g (30 mmol) of an aqueous solution of NaOH having a concentration of 28% by weight was added. The mixture was then stirred at 40° C. for 2.5 hours. Subsequently, the mixture was left to stand overnight, and was then again stirred at 40° C. for 3.5 hours. The reaction mixture was separated, and the thus obtained organic phase was washed sequentially with an aqueous solution of NaOH having a concentration of 1 mol/L and water. Following washing, the organic phase was concentrated using an evaporator, and the resulting residue was crystallized from methanol, yielding 6.08 g (14.8 mmol, yield: 99%) of white crystals.

The obtained white crystals exhibited the same physical property values as the compound labeled as compound number (3)-8 in Table 3 of WO 03/016303. The obtained white crystals were confirmed as being the compound represented by formula (q).

Example C2

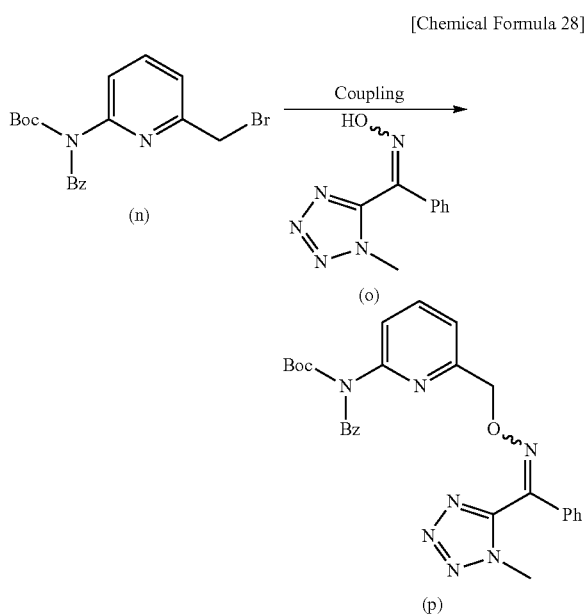

First, 0.47 g (1.28 mmol) of the compound represented by formula (n) was dissolved in 5 mL of acetonitrile, and then 0.2 g (1.4 mmol) of potassium carbonate was added thereto. Subsequently, 0.3 g (1.4 mmol) of the compound represented by formula (o) was added, and the mixture was stirred at room temperature for 30 minutes. The mixture was then left to stand overnight. Next, the reaction mixture was filtered and then concentrated under reduced pressure. The thus obtained residue was purified by column chromatography, yielding 300 mg (0.58 mmol, yield: 46%) of white crystals. The NMR measurement results for the thus obtained white crystals were as follows.

$^1$H-NMR (CDCl$_3$, δ ppm): 1.25 (s, 9H), 3.87 (s, 3H), 5.30 (s, 2H), 7.21 to 7.81 (m, 13H).

The obtained white crystals were confirmed as being the compound represented by formula (p).

Example C3

With the exception of replacing the compound represented by formula (n) with 2-(t-butoxycarbonylmethoxycarbonylamino)-6-bromomethyl-pyridine, the same procedure as the example C2 yielded a compound represented by formula (r). The NMR measurement results for the compound represented by formula (r) were as follows.

$^1$H-NMR (CDCl$_3$, δ ppm): 1.41 (s, 9H), 3.77 (s, 3H), 3.79 (s, 3H), 5.38 (s, 2H), 7.18 (d, 1H), 7.26 (d, 1H), 7.37 (m, 2H), 7.45 (m, 1H), 7.51 (m, 1H), 7.78 (t, 1H).

[Chemical Formula 29]

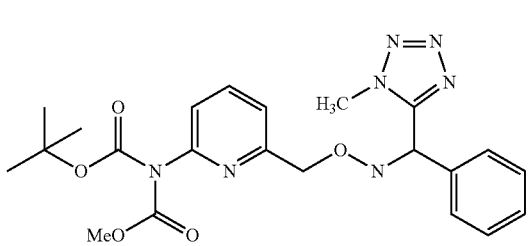

INDUSTRIAL APPLICABILITY

The compound containing a pyridine ring according to the present invention can be synthesized in an industrially advantageous manner, and is useful as an intermediate for producing tetrazolyloxime derivatives that exhibit fungicidal activity. Further, the production method according to the present invention enables 2-substituted amino-6-halomethylpyridine derivatives to be obtained with high selectivity and in high yield, and enables the production, in an industrially advantageous manner, of tetrazolyloxime derivatives that exhibit excellent antagonistic effects against plant diseases.

The invention claimed is:
1. A method for producing a halogenated picoline derivative represented by formula (3), the method comprising: a step B1 in which a compound represented by formula (2) and a halogenating agent are reacted in an organic solvent; and a step B2 in which a reaction product obtained in the step B1 is reduced,

[Chemical Formula 2]

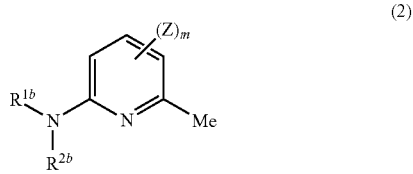

wherein $R^{1b}$ represents an unsubstituted or substituent-containing alkoxycarbonyl group,
$R^{2b}$ represents an unsubstituted or substituent-containing alkoxycarbonyl group, an unsubstituted or substituent-containing acyl group, an unsubstituted or substituent-containing aryloxycarbonyl group, or an unsubstituted or substituent-containing heterocyclic oxycarbonyl group,
Z represents a halogen atom, a cyano group, a nitro group, a hydroxyl group, a thiol group, a formyl group, a carboxyl group, an unsubstituted or substituent-containing amino group, an unsubstituted or substituent-containing alkyl group, an unsubstituted or substituent-containing alkenyl group, an unsubstituted or substituent-containing alkynyl group, an unsubstituted or substituent-containing aryl group, an unsubstituted or substituent-containing heterocyclic group, OR$^3$, S(O)$_p$R$^3$, COR$^3$ or CO$_2$R$^3$ (wherein R$^3$ represents an unsubstituted or substituent-containing amino group, an unsubstituted or substituent-containing alkyl group, an unsubstituted or substituent-containing alkenyl group, an unsubstituted or substituent-containing alkynyl group, an unsubstituted or substituent-containing aryl group, or an unsubstituted or substituent-containing heterocyclic group, and p represents a number of oxygen atoms in parentheses, and is an integer of 0 to 2), and
m represents a number of Z substituents and is an integer of 0 to 3, and when m is 2 or more, a plurality of the Z substituents may be identical to, or different from, each other,

[Chemical Formula 3]

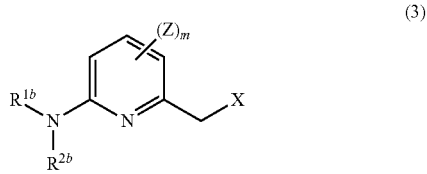

wherein $R^{1b}$, $R^{2b}$, Z and m are as defined above, and X represents a halogen atom.

2. The method for producing a halogenated picoline derivative according to claim 1, wherein the step B1 is performed in presence of a base.

3. The method for producing a halogenated picoline derivative according to claim 1 or 2, wherein the organic solvent in the step B1 is benzene or a halogenated hydrocarbon.

4. The method for producing a halogenated picoline derivative according to claim 1 or 3, wherein the step B2 is performed in presence of a phase transfer catalyst.

5. The method for producing a halogenated picoline derivative according to claim 1 or 3, wherein the halogenating agent is a brominating agent, and X represents a bromine atom.

* * * * *